US012195500B2

(12) United States Patent
Abnousi et al.

(10) Patent No.: US 12,195,500 B2
(45) Date of Patent: Jan. 14, 2025

(54) ANTIBODIES AGAINST DISEASE CAUSING AGENTS OF CANINES AND FELINES AND USES THEREOF

(71) Applicant: Novobind Livestock Therapeutics, Inc., Vancouver (CA)

(72) Inventors: Hamlet Abnousi, Vancouver (CA); Slade Andrew Loutet, Vancouver (CA); Filip Van Petegem, Vancouver (CA); Tsz Ying Sylvia Cheung, Vancouver (CA)

(73) Assignee: Novobind Livestock Therapeutics, Inc., Vancouver (CA)

( * ) Notice: Subject to any disclaimer, the term of this patent is extended or adjusted under 35 U.S.C. 154(b) by 503 days.

(21) Appl. No.: 17/292,160

(22) PCT Filed: Nov. 12, 2019

(86) PCT No.: PCT/IB2019/001196
§ 371 (c)(1),
(2) Date: May 7, 2021

(87) PCT Pub. No.: WO2020/099922
PCT Pub. Date: May 22, 2020

(65) Prior Publication Data
US 2022/0064224 A1    Mar. 3, 2022

Related U.S. Application Data

(60) Provisional application No. 62/760,765, filed on Nov. 13, 2018.

(51) Int. Cl.
*C07K 14/015*     (2006.01)
*A61P 31/12*      (2006.01)
*C12N 15/86*      (2006.01)
*A61K 38/00*      (2006.01)

(52) U.S. Cl.
CPC ............ *C07K 14/015* (2013.01); *A61P 31/12* (2018.01); *C12N 15/86* (2013.01); *A61K 38/00* (2013.01)

(58) Field of Classification Search
CPC ................ C07K 14/015; C07K 14/005; C07K 2317/22; C07K 2317/56; C07K 2317/76; C07K 16/081; C07K 2317/565; C07K 2317/569; A61P 31/12; C12N 15/86; C12N 2750/14322; C12N 2750/14323; A61K 38/00; A23K 50/40; A23K 20/14
See application file for complete search history.

(56) References Cited

U.S. PATENT DOCUMENTS

| 4,335,107 A | 6/1982 | Snoeyenbos et al. |
|---|---|---|
| 6,790,446 B2 | 9/2004 | Jacobs et al. |
| 8,637,025 B2 | 1/2014 | Robins-Browne et al. |
| 8,926,980 B2 | 1/2015 | Mitteness et al. |
| 11,130,800 B2 | 9/2021 | Abnousi |
| 2002/0106397 A1 | 8/2002 | Nash et al. |
| 2003/0003104 A1 | 1/2003 | Mottola et al. |
| 2007/0110758 A1 | 5/2007 | Campbell et al. |
| 2007/0280949 A1 | 12/2007 | Alfa |
| 2009/0191208 A1 | 7/2009 | Salzman et al. |
| 2009/0208506 A1 | 8/2009 | Rachamim et al. |
| 2014/0112938 A1 | 4/2014 | Robins-Browne et al. |
| 2015/0307597 A1 | 10/2015 | Arbabi Ghahroudi et al. |
| 2017/0183643 A1 | 6/2017 | Krogh et al. |
| 2017/0202242 A1 | 7/2017 | Blom et al. |
| 2017/0223986 A1 | 8/2017 | Schnorr |
| 2017/0240873 A1 | 8/2017 | Li et al. |
| 2021/0269512 A1 | 9/2021 | Abnousi et al. |
| 2022/0119506 A1 | 4/2022 | Abnousi et al. |

FOREIGN PATENT DOCUMENTS

| CN | 103665152 A | 3/2014 | |
|---|---|---|---|
| CN | 105884889 A | 8/2016 | |
| WO | WO-8600993 A1 | 2/1986 | |
| WO | WO-8601805 A1 | 3/1986 | |
| WO | WO-8604352 A1 | 7/1986 | |
| WO | WO-0140280 A2 | 6/2001 | |
| WO | WO-03070258 A1 | 8/2003 | |
| WO | WO-2004062551 A2 * | 7/2004 | ........... A61K 38/166 |
| WO | WO-2010079149 A1 | 7/2010 | |
| WO | 2012/164372 A1 | 12/2012 | |
| WO | WO-2015145250 A2 | 10/2015 | |
| WO | WO-2017199094 A1 | 11/2017 | |
| WO | WO-2020035741 A2 | 2/2020 | |
| WO | WO-2020099922 A1 | 5/2020 | |
| WO | WO-2020163284 A1 | 8/2020 | |
| WO | WO-2020234642 A1 | 11/2020 | |

(Continued)

OTHER PUBLICATIONS

Machine translation for CN 105884889 A retrieved from Google Patents on Nov. 8, 2022.
The Extended European Search Report issued from the European Patent Office on Oct. 4, 2022 in corresponding 19884610.7.
Abid et al.: Emerging threat of necrotic enteritis in poultry and its control without use of antibiotics: a review. The Journal of Animal and Plant Sciences. 26(6):1556-1567 (2016).
Boucher et al.: The apicomplexan glideosome and adhesins—structures and function. Journal of Structural Biology. 190(2):93-114 (2015).
Chapman: Milestones in avian coccidiosis research: a review. Poultry Science. 93(3):501-511 (2014).
EP19831311.6 Supplemental European Search Report dated Feb. 16, 2022.
EP19849450.2 Extended European Search Report dated Mar. 3, 2022.

(Continued)

*Primary Examiner* — Jeanette M Lieb
*Assistant Examiner* — Erinne R Dabkowski
(74) *Attorney, Agent, or Firm* — Smith, Gambrell & Russell, LLP; Judy Jarecki-Black; Sharon Ngwenya

(57) ABSTRACT

Described herein are methods and antibodies useful for reducing, eliminating, or preventing infection with a viral population in an animal. Also described herein are antigens useful for targeting by heavy chain antibodies and VHH fragments for reducing a viral population in an animal.

6 Claims, 3 Drawing Sheets

Specification includes a Sequence Listing.

(56) References Cited

FOREIGN PATENT DOCUMENTS

WO 2021/022067 A2 2/2021

OTHER PUBLICATIONS

Froelich et al., The interactions of Vibrio vulnificus and the oyster *Crassostrea virginica*. Microb Ecol. 65(4):807-816 (2013).

Garcia, E. Neutralizacion de la toxinas PirA y PirB de Vibrio parahaemolyticus asociado a AHPND con fragmentos de anticuerpos deplegados en fagos. Masters of Science Thesis, Centro de Investigaciones Biologicas del Noroeste S.C. Baja, Mexico (2016).

Keyburn et al.: NetB, a Pore-Forming Toxin from Necrotic Enteritis Strains of Clostridium perfringens. Toxins, Molecular Diversity Preservation International (MDPI) 2:1913-1927 (2010).

Lam et al., Nanobody-aided structure determination of the EpsI:EpsJ pseudopilin heterodimer from Vibrio vulnificus. J Struct Biol. 166(1):8-15 (2009).

Lee et al., The opportunistic marine pathogen Vibrio parahaemolyticus becomes virulent by acquiring a plasmid that expresses a deadly toxin. Proc Natl Acad Sci U S A 112(34):10798-10803 (2015).

Moore: Necrotic enteritis predisposing factors in broiler chickens. Avian Pathology. 45(3):275-281 (2016).

Unger et al.: Selection of Nanobodies that Block the Enzymatic and Cytotoxic Activities of the Binary Clostridium Difficile Toxin CDT. Scientific Reports. 5:7850 (2015).

Uzal et al.: Clostridium Perfringens Toxins Involved in Mammalian Veterinary Diseases. The Open Toxinology Journal. 3(1):24-42 (2013).

Van Meirhaeghe et al.: Coccidiosis a major threat to the chicken gut. Retrieved on May 25, 2018 from: https://www.poultryworld.net/Home/General/2014/9/Coccidiosis-a-major-threat-to-the-chicken-gut-1568808W/?dossier=35765&widgetid=1 (2014).

Wade et al.: The adherent abilities of Clostridium perfringensstrains are critical for the pathogenesis of avian necrotic enteritis. Veterinary Microbiology. Elsevier BV. 197:53-61 (2016).

Wade et al.: The true cost of necrotic enteritis. Retrieved on May 25, 2018 from: https://www.poultryworld.net/Meat/Articles/2015/10/The-true-cost-of-necrotic-enteritis-2699819W (2015).

Wangman et al., Development of monoclonal antibodies specific to ToxA and ToxB of Vibrio parahaemolyticus that cause acute hepatopancreatic necrosis disease (AHPND). Aquaculture 474:75-81 (2017).

Wesolowski et al.: 2009, "Single domain antibodies: promising experimental and therapeutic tools in infection and immunity," Med Microbiol Immunol. 198(3): 157-174.

Arbabi-Ghahroudi, Camelid single-domain antibodies: historical perspective and future outlook. Frontiers in Immunology 8:1589 [1-8] (2017).

Da Costa et al., Variable protection against experimental broiler necrotic enteritis after immunization with the C-terminal fragment of Clostridium perfringens alpha-toxin and a non-toxic NetB variant. Avian Pathology 45(3):381-388 (2016).

Ebrahimizadeh et al., Isolation and characterization of protective anti-LPS nanobody against V. cholerae O1 recognizing Inaba and Ogawa serotypes. Appl Microbiol Biotechnol. 97(10):4457-66. doi: 10.1007/s00253-012-4518-x (2013; epub 2012).

International Application No. PCT/IB2017/000684 International Preliminary Report on Patentability dated Nov. 20, 2018.

International Application No. PCT/IB2017/000684 International Search Report and Written Opinion of the International Searching Authority dated Oct. 11, 2017.

Keyburn et al., Vaccination with recombinant NetB toxin partially protects broiler chickens from necrotic enteritis. Veterinary Research 44:54 [1-8] (2013).

Mcclain et al., Functional analysis of neutralizing antibodies against Clostridium perfringens epsilon-toxin. Infection and Immunity 75(4):1785-1793 (2007).

Muyldermans et al.: Sequence and structure of VH domain from naturally occurring camel heavy chain immunoglobulins lacking light chains. Protein Engineering. 7(9):1125-1135 (1994) Abstract Only.

Nowacka: Isolation of Salmonella Serovar-Specific Single Domain Antibodies, A Thesis Presented to The University of Guelph, Ontario, Canada, https://atrium.lib.uoguelph.ca/xmlui/handle/10214/8503 (2014).

PCT/IB2019/000687 International Preliminary Report on Patentability dated Dec. 18, 2020.

PCT/IB2019/000687 International Search Report and Written Opinion dated Dec. 12, 2019.

PCT/IB2019/001196 International Search Report and Written Opinion dated Mar. 18, 2020.

PCT/IB2019/001198 International Invitation to Pay Additional Fees dated Jan. 17, 2020.

PCT/IB2019/001198 International Preliminary Report on Patentability dated Jan. 15, 2021.

PCT/IB2019/001198 International Search Report and Written Opinion dated Mar. 20, 2020.

PCT/IB2020/000380 International Search Report and Written Opinion dated Aug. 28, 2020.

Sato et al., Monoclonal antibodies against alpha toxin of Clostridium perfringens. FEMS Microbiol Lett. 50(1-2):173-176 (1989).

U.S. Appl. No. 16/300,457 Final Office Action dated Feb. 1, 2021.

U.S. Appl. No. 16/300,457 Office Action dated Jul. 30, 2020.

Wu et al., Panning anti-LPS nanobody as a capture target to enrich Vibrio fluvialis. Biochem Biophys Res Commun. 512(3):531-536. doi: 10.1016/j.bbrc.2019.03.104 (2019).

Yuan et al.: Comparison of two single-chain antibodies that neutralize canine parvovirus: analysis of an antibody-combining site and mechanisms of neutralization. Virology. 269(2):471-480 (2000).

Zeng et al., The generation and characterization of recombinant protein and antibodies of clostridium perfringens beta2 toxin. Journal of Immunological Research 2016:5708468 [1-12] (2016).

Rudikoff, et al., "Single amino acid substitution altering antigen-binding specificity," Proc. Nat. Acad. Sci. 79(6): 1979-1983 (1982).

Tamura, et al., "Structural Correlates of an Anticarcinoma Antibody: Identification of Specificity-Determining Residues (SDRs) and Development of a Minimally Immunogenic Antibody Variant by Retention of SDRs Only," J Immunol, 164 (3): 1432-1441 (2000).

International Preliminary Report on Patentability issued May 18, 2021 in International Patent Application No. PCT/IB2019/001196 (6 pages).

Partial Supplementary European Search Report issued Jun. 30, 2022 in European Patent Application No. EP 19884610 (13 pages).

Office Action issued Jan. 17, 2024 in Canadian Patent Application No. 3,118,819 (6 pages).

* cited by examiner

SEQUENCE LISTING

<160> NUMBER OF SEQ ID NOS: 92

<210> SEQ ID NO 1
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Val Ser Gly Leu Ala Phe Gly Arg Val
            20                  25                  30

Ala Met Ala Trp Tyr Arg Gln Ala Pro Gly Lys Glu Arg Glu Leu Val
        35                  40                  45

Ala Arg Ile Ser Ser Gly Gly Tyr Thr Asn Tyr Ala Asp Ser Ala Lys
    50                  55                  60

Gly Arg Phe Thr Ile Ser Arg Asp Asn Val Lys Asn Leu Val Tyr Leu
65                  70                  75                  80

Gln Met Asn Ser Leu Lys Phe Asp Asp Thr Ala Val Tyr Tyr Cys Asn
                85                  90                  95

Ser Gly Trp Ser Gly Asp Tyr Trp Gly Lys Gly Thr Leu Val Thr Val
            100                 105                 110

Ser Ser

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Ser Tyr
            20                  25                  30

Ala Met Gly Trp Phe Arg Gln Ala Pro Gly Lys Glu Arg Glu Tyr Val
        35                  40                  45

Ala Ala Ile Asn Arg Phe Ser Gly Thr Tyr Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ser Arg Ile Leu Gly Leu Ser Thr Ala Arg Glu Asp Tyr Asn Tyr
            100                 105                 110

Trp Gly Gln Gly Thr Gln Val Thr Val Ser Ser
        115                 120

<210> SEQ ID NO 3
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Ala Ala Ser Gly His Thr Phe Ser Ser Asn
            20                  25                  30

Thr Met Ala Trp Phe Arg Gln Ala Pro Gly Lys Glu Arg Glu Leu Val
        35                  40                  45

Ala Val Ile Gly Trp Ile Gly Ser Thr Tyr Tyr Ala Asp Ser Val
    50                  55                  60

Lys Gly Arg Phe Thr Ile Ser Arg Asp Asn Thr Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Ala Ser Arg Arg Arg Phe Ser Leu Gln Tyr Val Asp Tyr
            100                 105                 110

Thr Tyr Trp Gly Gln Gly Thr Gln Val Thr Val Ser Ser
        115                 120                 125

<210> SEQ ID NO 4
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Arg Ala Ser Gly Arg Thr Phe Ser Ser Ser
            20                  25                  30

Ser Met Gly Trp Phe Arg Gln Ala Pro Gly Lys Glu Arg Asp Phe Val
        35                  40                  45

Ala Ala Ile Ser Trp Asp Gly Ala Ser Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Thr Met Asp Phe Ile Val Leu Leu Thr Lys Trp Tyr Pro
            100                 105                 110

Tyr Trp Gly Gln Gly Thr Gln Val Thr Val Ser Ser
        115                 120

<210> SEQ ID NO 5
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

```
Ala Met Gly Trp Phe Arg Gln Ala Pro Gly Lys Glu Arg Glu Tyr Val
            35                  40                  45

Ala Ala Ile Asn Arg Phe Gly Gly Thr Tyr Tyr Ala Asp Phe Val Lys
 50                      55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Ser Arg Ile Leu Gly Leu Thr Thr Ala Arg Glu Asp Tyr Asn Tyr
             100                 105                 110

Trp Gly Gln Gly Thr Gln Val Thr Val Ser Ser
        115                 120
```

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Ser
             20                  25                  30

Ser Met Gly Trp Phe Arg Gln Ala Pro Gly Lys Glu Arg Asp Phe Val
            35                  40                  45

Ala Ala Ile Asn Trp Ser Gly Asp Ser Thr Arg Tyr Ala Asp Ser Val
 50                      55                  60

Lys Gly Arg Phe Thr Ile Ser Arg Asp Asn Ala Lys Ser Thr Val Tyr
 65                  70                  75                  80

Leu Gln Met Asn Ser Leu Lys Pro Glu Asp Thr Ala Val Tyr Tyr Cys
                 85                  90                  95

Ala Ala Ser Thr Met Asp Phe Ile Val Leu Leu Thr Lys Trp Tyr Pro
             100                 105                 110

Tyr Trp Gly Gln Gly Thr Gln Val Thr Val Ser Ser
        115                 120
```

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Val Gln Leu Gln Glu Ser Gly Gly Gly Leu Val Gln Pro Gly Gly
 1               5                  10                  15

Ser Leu Arg Leu Ser Cys Ala Ala Ser Gly Ser Ile Phe Ser Ile Asn
             20                  25                  30

Val Met Ala Trp Tyr Arg Gln Ala Pro Gly Lys Glu Arg Glu Tyr Val
            35                  40                  45

Ala Ser Ile Thr Arg Gly Gly Asp Tyr Tyr Ala Asn Ser Val Lys
 50                      55                  60

Gly Arg Phe Thr Ile Ser Arg Asp Asn Ala Lys Asn Ala Val Tyr Leu
 65                  70                  75                  80
```

Gln Met Asn Ser Leu Lys Pro Glu Asp Thr Ala Val Tyr Glu Cys Asn
            85                  90                  95

Ala Gln Ile Ser Gln Thr Ile Ser Gly Asp Tyr Arg Asn Tyr Trp Gly
            100                 105                 110

Gln Gly Thr Gln Val Thr Val Ser Ser
        115                 120

<210> SEQ ID NO 8
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Tyr Val
            35                  40                  45

Ala Ala Ile Asn Arg Phe Gly Gly Thr Tyr Tyr Ala Asp Phe Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
            85                  90                  95

Ala Ser Thr Ile Leu Gly Leu Thr Thr Val Arg Glu Asp Tyr Asn Tyr
            100                 105                 110

Trp Gly Gln Gly Thr Gln Val Thr Val Ser Ser
            115                 120

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Gly Met Gly Trp Phe Arg Gln Ala Pro Gly Lys Glu Arg Glu Tyr Val
            35                  40                  45

Ala Val Ile Asn Arg Phe Gly Gly Thr Tyr Tyr Ala Asp Phe Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
            85                  90                  95

Ala Ser Arg Ile Leu Gly Leu Ser Thr Ala Arg Glu Asp Tyr Asn Tyr
            100                 105                 110

Trp Gly Gln Gly Thr Gln Val Thr Val Ser Ser
            115                 120

```
<210> SEQ ID NO 10
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Ser Gly Gly Gly Leu Val Gln Pro Gly Gly
1               5                   10                  15

Ser Leu Arg Leu Ser Cys Ala Val Ser Gly Leu Ala Phe Gly Arg Tyr
            20                  25                  30

Ala Met Ala Trp Tyr Arg Gln Ala Pro Gly Lys Glu Arg Glu Leu Val
        35                  40                  45

Ala Arg Ile Ser Asn Gly Gly Tyr Thr Asn Tyr Ala Asp Ser Ala Lys
    50                  55                  60

Gly Arg Phe Thr Ile Ser Arg Asp Asn Val Lys Asn Thr Val Tyr Leu
65                  70                  75                  80

Glu Met Asn Ser Leu Lys Phe Asp Asp Thr Ala Val Tyr Tyr Cys Asn
                85                  90                  95

Ser Gly Trp Ser Gly Asn Tyr Trp Gly Lys Gly Thr Leu Val Thr Val
            100                 105                 110

Ser Ser

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Ser Ser Ile Tyr
            20                  25                  30

Val Met Gly Trp Tyr Arg Gln Ala Pro Gly Lys Pro Arg Asp Leu Val
        35                  40                  45

Ala Ser Ile Asn Gly Gly Thr Thr Asn Tyr Ala Asn Ser Val Lys Gly
    50                  55                  60

Arg Phe Thr Ile Ser Arg Asp Asn Ala Lys Asn Thr Val Ser Leu Gln
65                  70                  75                  80

Met Asn Thr Leu Lys Pro Glu Asp Thr Ala Val Tyr Tyr Cys Asn Ala
                85                  90                  95

Arg His Ser Ser Trp Arg Asp Tyr Trp Gly Gln Gly Thr Gln Val
            100                 105                 110

Thr Val Ser Ser
        115

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
Gln Val Gln Leu Gln Glu Ser Gly Gly Gly Leu Val Gln Ala Gly Gly
1               5                   10                  15

Ser Leu Arg Leu Ser Cys Ala Ile Pro Gly Arg Thr Phe Arg Asn Tyr
            20                  25                  30

Val Met Gly Trp Phe Arg Gln Ala Pro Gly Lys Glu Arg Glu Phe Val
        35                  40                  45

Ala Ala Ile Ser Arg Ser Gly Gly Ser Thr Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Met Leu Lys Pro Glu Asp Thr Ala Val Tyr Tyr Cys
                85                  90                  95

Ala Ala Ser Tyr Ser Ile Met Gln Pro Thr Thr Ala Ser Ala Met Asp
            100                 105                 110

Tyr Trp Gly Lys Gly Thr Leu Val Thr Val Ser Ser
        115                 120
```

<210> SEQ ID NO 13
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Gln Gln Ser Gly Gly Gly Ser Val Gln Ala Gly Gly
1               5                   10                  15

Ser Leu Ser Val Ser Cys Ala Pro Ser Gly Arg Thr Phe Ser Trp Asn
            20                  25                  30

Ala Ile Gly Trp Phe Arg Gln Ala Pro Gly Lys Glu Arg Glu Phe Val
        35                  40                  45

Ala Ala Ile Arg Leu Ser Thr Gly Trp Thr Ser Tyr Ala Asp Ser Val
    50                  55                  60

Lys Gly Arg Phe Ser Ile Ser Arg Asp Ala Ala Lys Thr Thr Ala Tyr
65                  70                  75                  80

Leu Gln Met Asn Ser Leu Lys Pro Glu Asp Thr Ala Val Tyr Tyr Cys
                85                  90                  95

Ala Ala Asp Arg Glu Gly Ser Ile Ala Thr Met Thr Arg Asp Tyr Glu
            100                 105                 110

Tyr Asp Tyr Trp Gly Gln Gly Thr Gln Val Thr Val Ser Ser
        115                 120                 125
```

<210> SEQ ID NO 14
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Tyr Val
        35                  40                  45
```

Ala Gly Ile Asn Arg Phe Gly Gly Thr Tyr Tyr Ala Asp Phe Val Gln
         50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                 85                  90                  95

Ala Ser Arg Ile Leu Gly Leu Thr Thr Val Arg Glu Asp Tyr Asn Tyr
            100                 105                 110

Trp Gly Gln Gly Thr Gln Val Thr Val Ser Ser
            115                 120

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ile Gly Asp Arg Pro Tyr
            20                  25                  30

Val Met Ala Trp His Arg Gln Ala Pro Gly Lys Gln Arg Glu Leu Val
        35                  40                  45

Ala Thr Ile Thr Arg Asp Gly Tyr Thr Asn Tyr Ala Asp Thr Val Lys
    50                  55                  60

Gly Arg Phe Val Val Ser Arg Asp Asn Ala Gln Asn Thr Val Tyr Leu
65                  70                  75                  80

Gln Met Asn Tyr Leu Lys Pro Ala Asp Thr Ala Val Tyr Tyr Cys Arg
                85                  90                  95

Ala Tyr Asn Ala Tyr Leu Asn Leu Gly Tyr Trp Gly Gln Gly Thr Gln
            100                 105                 110

Val Thr Val Ser Thr
            115

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Ser Thr Phe
            20                  25                  30

Ala Met Gly Trp Tyr Arg Gln Ala Pro Gly Lys Gln Arg Glu Leu Val
        35                  40                  45

Ala Gln Ile Ser Asn Asp Gly Tyr Ile Asn Tyr Ala Asp Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Asp Asp Thr Ala Val Tyr Ser Cys Arg
                85                  90                  95

Ala Gly Thr Phe Tyr Trp Gly Gln Gly Thr Gln Val Thr Val Ser Ser
            100                 105                 110

<210> SEQ ID NO 17
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Ser Ser Ile Asn
            20                  25                  30

His Ile Ala Trp Tyr Arg Gln Ala Pro Gly Lys Gln Arg Glu Trp Val
        35                  40                  45

Ala Thr Ile Thr Ser Gly Gly Ser Thr Tyr Tyr Thr Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Lys Ala Asn Gln Ala Ala Gly Asn Lys Asp Tyr Trp Gly Gln Gly Thr
            100                 105                 110

Gln Val Thr Val Ser Ser
        115

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Tyr Val
        35                  40                  45

Ala Ala Ile Asn Arg Phe Gly Gly Thr Tyr Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ser Gly Ile Leu Gly Leu Ser Thr Ala Arg Glu Asp Tyr Asn Tyr
            100                 105                 110

Trp Gly Gln Gly Thr Gln Val Thr Val Ser Ser
        115                 120

<210> SEQ ID NO 19
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 19

Gly Leu Ala Phe Gly Arg Val Ala Met
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Arg Thr Phe Ser Ser Tyr Ala Met
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly His Thr Phe Ser Ser Asn Thr Met
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Arg Thr Phe Ser Ser Ser Ser Met
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Arg Thr Phe Ser Ser Tyr Ala Met
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Arg Thr Phe Ser Ser Ser Ser Met
1               5
```

```
<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Ile Phe Ser Ile Asn Val Met
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Arg Thr Phe Ser Ser Tyr Ala Met
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Arg Thr Phe Ser Ser Tyr Gly Met
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Leu Ala Phe Gly Arg Tyr Ala Met
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Thr Ser Ser Ile Tyr Val Met
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Gly Arg Thr Phe Arg Asn Tyr Val Met
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Arg Thr Phe Ser Trp Asn Ala Ile
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Arg Thr Phe Ser Ser Tyr Ala Met
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ile Gly Asp Arg Pro Tyr Val Met
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ile Thr Phe Ser Thr Phe Ala Met
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ser Thr Ser Ser Ile Asn His Ile
1               5

<210> SEQ ID NO 36
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 36

Gly Arg Thr Phe Ser Ser Tyr Ala Met
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Ser Ser Gly Gly Tyr Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Asn Arg Phe Ser Gly Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Gly Trp Ile Gly Gly Ser Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Ser Trp Asp Gly Ala Ser Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Asn Arg Phe Gly Gly Thr
1               5
```

```
<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Trp Ser Gly Asp Ser Thr
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Thr Arg Gly Gly Gly Asp
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Asn Arg Phe Gly Gly Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Asn Arg Phe Gly Gly Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Ser Asn Gly Gly Tyr Thr
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Ile Asn Gly Gly Thr Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Ser Arg Ser Gly Gly Ser Thr
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Arg Leu Ser Thr Gly Trp Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Asn Arg Phe Gly Gly Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Thr Arg Asp Gly Tyr Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Ser Asn Asp Gly Tyr Ile
1               5

<210> SEQ ID NO 53
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ile Thr Ser Gly Gly Gly Ser Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Asn Arg Phe Gly Gly Thr
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Ser Gly Trp Ser Gly Asp Tyr
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ala Ser Arg Ile Leu Gly Leu Ser Thr Ala Arg Glu Asp Tyr Asn
1               5                   10                  15

Tyr

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Ala Asp Ala Ser Arg Arg Arg Phe Ser Leu Gln Tyr Val Asp Tyr
1               5                   10                  15

Thr Tyr

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 58

Ala Ala Asp Ala Ser Arg Arg Arg Phe Ser Leu Gln Tyr Val Asp Tyr
1               5                   10                  15

Thr Tyr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ala Ser Arg Ile Leu Gly Leu Thr Thr Ala Arg Glu Asp Tyr Asn
1               5                   10                  15

Tyr

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ala Ser Thr Met Asp Phe Ile Val Leu Leu Thr Lys Trp Tyr Pro
1               5                   10                  15

Tyr

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Ala Gln Ile Ser Gln Thr Ile Ser Gly Asp Tyr Arg Asn Tyr
1               5                   10                  15

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ala Ser Thr Ile Leu Gly Leu Thr Thr Val Arg Glu Asp Tyr Asn
1               5                   10                  15

Tyr

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 63

Ala Ala Ser Arg Ile Leu Gly Leu Ser Thr Ala Arg Glu Asp Tyr Asn
1               5                   10                  15

Tyr

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Ser Gly Trp Ser Gly Asn Tyr
1               5

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Ala Arg His Ser Ser Ser Trp Arg Asp Tyr
1               5                   10

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ala Ser Tyr Ser Ile Met Gln Pro Thr Thr Ala Ser Ala Met Asp
1               5                   10                  15

Tyr

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Ala Asp Arg Glu Gly Ser Ile Ala Thr Met Thr Arg Asp Tyr Glu
1               5                   10                  15

Tyr Asp Tyr

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ala Ser Arg Ile Leu Gly Leu Thr Thr Val Arg Glu Asp Tyr Asn
1               5                   10                  15
```

```
1               5                  10                  15
Tyr

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ala Tyr Asn Ala Tyr Leu Asn Leu Gly Tyr
1               5                  10

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Ala Gly Thr Phe Tyr
1               5

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Ala Asn Gln Ala Ala Gly Asn Lys Asp Tyr
1               5                  10

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ala Ser Gly Ile Leu Gly Leu Ser Thr Ala Arg Glu Asp Tyr Asn
1               5                  10                  15

Tyr

<210> SEQ ID NO 73
<211> LENGTH: 727
<212> TYPE: PRT
<213> ORGANISM: Canine parvovirus 2c

<400> SEQUENCE: 73

Met Ala Pro Pro Ala Lys Arg Ala Arg Arg Gly Leu Val Pro Pro Gly
1               5                  10                  15

Tyr Lys Tyr Leu Gly Pro Gly As

```
Tyr Leu Arg Ser Gly Lys Asn Pro Tyr Leu Tyr Phe Ser Pro Ala Asp
 50                  55                  60

Gln Arg Phe Ile Asp Gln Thr Lys Asp Ala Lys Asp Trp Gly Gly Lys
 65                  70                  75                  80

Ile Gly His Tyr Phe Phe Arg Ala Lys Lys Ala Ile Ala Pro Val Leu
                 85                  90                  95

Thr Asp Thr Pro Asp His Pro Ser Thr Ser Arg Pro Thr Lys Pro Thr
                100                 105                 110

Lys Arg Ser Lys Pro Pro His Ile Phe Ile Asn Leu Ala Lys Lys
                115                 120                 125

Lys Lys Ala Gly Ala Gly Gln Val Lys Arg Asp Asn Leu Ala Pro Met
130                 135                 140

Ser Asp Gly Ala Val Gln Pro Asp Gly Gly Gln Pro Ala Val Arg Asn
145                 150                 155                 160

Glu Arg Ala Thr Gly Ser Gly Asn Gly Ser Gly Gly Gly Gly Gly Gly
                165                 170                 175

Gly Ser Gly Gly Val Gly Ile Ser Thr Gly Thr Phe Asn Asn Gln Thr
                180                 185                 190

Glu Phe Lys Phe Leu Glu Asn Gly Trp Val Glu Ile Thr Ala Asn Ser
                195                 200                 205

Ser Arg Leu Val His Leu Asn Met Pro Glu Ser Glu Asn Tyr Arg Arg
210                 215                 220

Val Val Val Asn Asn Leu Asp Lys Thr Ala Val Asn Gly Asn Met Ala
225                 230                 235                 240

Leu Asp Asp Thr His Ala Gln Ile Val Thr Pro Trp Ser Leu Val Asp
                245                 250                 255

Ala Asn Ala Trp Gly Val Trp Phe Asn Pro Gly Asp Trp Gln Leu Ile
                260                 265                 270

Val Asn Thr Met Ser Glu Leu His Leu Val Ser Phe Glu Gln Glu Ile
                275                 280                 285

Phe Asn Val Val Leu Lys Thr Val Ser Glu Ser Ala Thr Gln Pro Pro
290                 295                 300

Thr Lys Val Tyr Asn Asn Asp Leu Thr Ala Ser Leu Met Val Ala Leu
305                 310                 315                 320

Asp Ser Asn Asn Thr Met Pro Phe Thr Pro Ala Ala Met Arg Ser Glu
                325                 330                 335

Thr Leu Gly Phe Tyr Pro Trp Lys Pro Thr Ile Pro Thr Pro Trp Arg
                340                 345                 350

Tyr Tyr Phe Gln Trp Asp Arg Thr Leu Ile Pro Ser His Thr Gly Thr
                355                 360                 365

Ser Gly Thr Pro Thr Asn Ile Tyr His Gly Thr Asp Pro Asp Asp Val
                370                 375                 380

Gln Phe Tyr Thr Ile Glu Asn Ser Val Pro Val His Leu Leu Arg Thr
385                 390                 395                 400

Gly Asp Glu Phe Ala Thr Gly Thr Phe Phe Asp Cys Lys Pro Cys
                405                 410                 415

Arg Leu Thr His Thr Trp Gln Thr Asn Arg Ala Leu Gly Leu Pro Pro
                420                 425                 430

Phe Leu Asn Ser Leu Pro Gln Ala Glu Gly Gly Thr Asn Phe Gly Tyr
                435                 440                 445

Ile Gly Val Gln Gln Asp Lys Arg Arg Gly Val Thr Gln Met Gly Asn
450                 455                 460

Thr Asn Tyr Ile Thr Glu Ala Thr Ile Met Arg Pro Ala Glu Val Gly
```

```
                465                 470                 475                 480
Tyr Ser Ala Pro Tyr Tyr Ser Phe Glu Ala Ser Thr Gln Gly Pro Phe
                    485                 490                 495
Lys Thr Pro Ile Ala Ala Gly Arg Gly Gly Ala Gln Thr Asp Glu Asn
                500                 505                 510
Gln Ala Ala Asp Gly Asp Pro Arg Tyr Ala Phe Gly Arg Gln His Gly
                515                 520                 525
Gln Lys Thr Thr Thr Thr Gly Glu Thr Pro Glu Arg Phe Thr Tyr Ile
            530                 535                 540
Ala His Gln Asp Thr Gly Arg Tyr Pro Glu Gly Asp Trp Ile Gln Asn
545                 550                 555                 560
Ile Asn Phe Asn Leu Pro Val Thr Glu Asp Asn Val Leu Leu Pro Thr
                    565                 570                 575
Asp Pro Ile Gly Gly Lys Thr Gly Ile Asn Tyr Thr Asn Ile Phe Asn
                580                 585                 590
Thr Tyr Gly Pro Leu Thr Ala Leu Asn Asn Val Pro Pro Val Tyr Pro
            595                 600                 605
Asn Gly Gln Ile Trp Asp Lys Glu Phe Asp Thr Asp Leu Lys Pro Arg
        610                 615                 620
Leu His Val Asn Ala Pro Phe Val Cys Gln Asn Asn Cys Pro Gly Gln
625                 630                 635                 640
Leu Phe Val Lys Val Ala Pro Asn Leu Thr Asn Glu Tyr Asp Pro Asp
                    645                 650                 655
Ala Ser Ala Asn Met Ser Arg Ile Val Thr Tyr Ser Asp Phe Trp Trp
                660                 665                 670
Lys Gly Lys Leu Val Phe Lys Ala Lys Leu Arg Ala Ser His Thr Trp
            675                 680                 685
Asn Pro Ile Gln Gln Met Ser Ile Asn Val Asp Asn Gln Phe Asn Tyr
        690                 695                 700
Val Pro Ser Asn Ile Gly Gly Met Lys Ile Val Tyr Glu Lys Ser Gln
705                 710                 715                 720
Leu Ala Pro Arg Lys Leu Tyr
                725

<210> SEQ ID NO 74
<211> LENGTH: 727
<212> TYPE: PRT
<213> ORGANISM: Feline panleukopenia virus

<400> SEQUENCE: 74

Met Ala Pro Pro Ala Lys Arg Ala Arg Arg Gly Leu Val Pro Pro Gly
1               5                   10                  15
Tyr Lys Tyr Leu Gly Pro Gly Asn Ser Leu Asp Gln Gly Glu Pro Thr
                20                  25                  30
Asn Pro Ser Asp Ala Ala Ala Lys Glu His Asp Glu Ala Tyr Ala Ala
            35                  40                  45
Tyr Leu Arg Ser Gly Lys Asn Pro Tyr Leu Tyr Phe Ser Pro Ala Asp
        50                  55                  60
Gln Arg Phe Ile Asp Gln Thr Lys Asp Ala Lys Asp Trp Gly Gly Lys
65                  70                  75                  80
Ile Gly His Tyr Phe Phe Arg Ala Lys Lys Ala Ile Ala Pro Val Leu
                85                  90                  95
Thr Asp Thr Pro Asp His Pro Ser Thr Ser Arg Pro Thr Lys Pro Thr
                100                 105                 110
```

-continued

```
Lys Arg Ser Lys Pro Pro His Ile Phe Ile Asn Leu Ala Lys Lys
            115                 120                 125
Lys Lys Ala Gly Ala Gly Gln Val Lys Arg Asp Asn Leu Ala Pro Met
130             135                 140
Ser Asp Gly Ala Val Gln Pro Asp Gly Gln Pro Ala Val Arg Asn
145                 150                 155                 160
Glu Arg Ala Thr Gly Ser Gly Asn Ser Gly Gly Gly Gly Gly
                165                 170                 175
Gly Ser Gly Gly Val Gly Ile Ser Thr Gly Thr Phe Asn Asn Gln Thr
            180                 185                 190
Glu Phe Lys Phe Leu Glu Asn Gly Trp Val Glu Ile Thr Ala Asn Ser
                195                 200                 205
Ser Arg Leu Val His Leu Asn Met Pro Glu Ser Glu Asn Tyr Lys Arg
210                 215                 220
Val Val Val Asn Asn Met Asp Lys Thr Ala Val Lys Gly Asn Met Ala
225                 230                 235                 240
Leu Asp Asp Ile His Val Gln Ile Val Thr Pro Trp Ser Leu Val Asp
                245                 250                 255
Ala Asn Ala Trp Gly Val Trp Phe Asn Pro Gly Asp Trp Gln Leu Ile
            260                 265                 270
Val Asn Thr Met Ser Glu Leu His Leu Val Ser Phe Glu Gln Glu Ile
        275                 280                 285
Phe Asn Val Val Leu Lys Thr Val Ser Glu Ser Ala Thr Gln Pro Pro
        290                 295                 300
Thr Lys Val Tyr Asn Asn Asp Leu Thr Ala Ser Leu Met Val Ala Leu
305                 310                 315                 320
Asp Ser Asn Asn Thr Met Pro Phe Thr Pro Ala Ala Met Arg Ser Glu
                325                 330                 335
Thr Leu Gly Phe Tyr Pro Trp Lys Pro Thr Ile Pro Thr Pro Trp Arg
            340                 345                 350
Tyr Tyr Phe Gln Trp Asp Arg Thr Leu Ile Pro Ser His Thr Gly Thr
        355                 360                 365
Ser Gly Thr Pro Thr Asn Val Tyr His Gly Thr Asp Pro Asp Asp Val
370                 375                 380
Gln Phe Tyr Thr Ile Glu Asn Ser Val Pro Val His Leu Leu Arg Thr
385                 390                 395                 400
Gly Asp Glu Phe Ala Thr Gly Thr Phe Phe Phe Asp Cys Lys Pro Cys
                405                 410                 415
Arg Leu Thr His Thr Trp Gln Thr Asn Arg Ala Leu Gly Leu Pro Pro
            420                 425                 430
Phe Leu Asn Ser Leu Pro Gln Ser Glu Gly Ala Thr Asn Phe Gly Asp
        435                 440                 445
Ile Gly Val Gln Gln Asp Lys Arg Arg Gly Val Thr Gln Met Gly Asn
450                 455                 460
Thr Asp Tyr Ile Thr Glu Ala Thr Ile Met Arg Pro Ala Glu Val Gly
465                 470                 475                 480
Tyr Ser Ala Pro Tyr Tyr Ser Phe Glu Ala Ser Thr Gln Gly Pro Phe
                485                 490                 495
Lys Thr Pro Ile Ala Ala Gly Arg Gly Gly Ala Gln Thr Asp Glu Asn
            500                 505                 510
Gln Ala Ala Asp Gly Asp Pro Arg Tyr Ala Phe Gly Arg Gln His Gly
        515                 520                 525
Gln Lys Thr Thr Thr Thr Gly Glu Thr Pro Glu Arg Phe Thr Tyr Ile
```

```
                530             535             540
Ala His Gln Asp Thr Gly Arg Tyr Pro Glu Gly Asp Trp Ile Gln Asn
545                 550                 555                 560

Ile Asn Phe Asn Leu Pro Val Thr Asn Asp Asn Val Leu Leu Pro Thr
                565                 570                 575

Asp Pro Ile Gly Gly Lys Thr Gly Ile Asn Tyr Thr Asn Ile Phe Asn
                580                 585                 590

Thr Tyr Gly Pro Leu Thr Ala Leu Asn Asn Val Pro Pro Val Tyr Pro
            595                 600                 605

Asn Gly Gln Ile Trp Asp Lys Glu Phe Asp Thr Asp Leu Lys Pro Arg
            610                 615                 620

Leu His Val Asn Ala Pro Phe Val Cys Gln Asn Asn Cys Pro Gly Gln
625                 630                 635                 640

Leu Phe Val Lys Val Ala Pro Asn Leu Thr Asn Glu Tyr Asp Pro Asp
                645                 650                 655

Ala Ser Ala Asn Met Ser Arg Ile Val Thr Tyr Ser Asp Phe Trp Trp
                660                 665                 670

Lys Gly Lys Leu Val Phe Lys Ala Lys Leu Arg Ala Ser His Thr Trp
                675                 680                 685

Asn Pro Ile Gln Gln Met Ser Ile Asn Val Asp Asn Gln Phe Asn Tyr
690                 695                 700

Val Pro Asn Asn Ile Gly Ala Met Lys Ile Val Tyr Glu Lys Ser Gln
705                 710                 715                 720

Leu Ala Pro Arg Lys Leu Tyr
                725

<210> SEQ ID NO 75
<211> LENGTH: 727
<212> TYPE: PRT
<213> ORGANISM: Canine parvovirus 2a

<400> SEQUENCE: 75

Met Ala Pro Pro Ala Lys Arg Ala Arg Arg Gly Leu Val Pro Pro Gly
1               5                   10                  15

Tyr Lys Tyr Leu Gly Pro Gly Asn Ser Leu Asp Gln Gly Glu Pro Thr
                20                  25                  30

Asn Pro Ser Asp Ala Ala Ala Lys Glu His Asp Glu Ala Tyr Ala Ala
            35                  40                  45

Tyr Leu Arg Ser Gly Lys Asn Pro Tyr Leu Tyr Phe Ser Pro Ala Asp
50                  55                  60

Gln Arg Phe Ile Asp Gln Thr Lys Asp Ala Lys Asp Trp Gly Gly Lys
65                  70                  75                  80

Ile Gly His Tyr Phe Phe Arg Ala Lys Lys Ala Ile Ala Pro Val Leu
                85                  90                  95

Thr Asp Thr Pro Asp His Pro Ser Thr Ser Arg Pro Thr Lys Pro Thr
                100                 105                 110

Lys Arg Ser Arg Pro Pro Pro His Ile Phe Ile Asn Leu Ala Lys Lys
            115                 120                 125

Lys Lys Ala Gly Ala Gly Gln Val Lys Arg Asp Asn Leu Ala Pro Met
130                 135                 140

Ser Asp Gly Ala Val Gln Pro Asp Gly Gly Gln Pro Ala Val Arg Asn
145                 150                 155                 160

Glu Arg Ala Thr Gly Ser Gly Asn Gly Ser Gly Gly Gly Gly Gly Gly
                165                 170                 175
```

```
Gly Ser Gly Gly Val Gly Ile Ser Thr Gly Thr Phe Asn Asn Gln Thr
            180                 185                 190

Glu Phe Lys Phe Leu Glu Asn Gly Trp Val Glu Ile Thr Ala Asn Ser
        195                 200                 205

Ser Arg Leu Val His Leu Asn Met Pro Glu Ser Glu Asn Tyr Arg Arg
    210                 215                 220

Val Val Val Asn Asn Leu Asp Lys Thr Ala Val Asn Gly Asn Met Ala
225                 230                 235                 240

Leu Asp Asp Thr His Ala Gln Ile Val Thr Pro Trp Ser Leu Val Asp
                245                 250                 255

Ala Asn Ala Trp Gly Val Trp Phe Asn Pro Gly Asp Trp Gln Leu Ile
            260                 265                 270

Val Asn Thr Met Ser Glu Leu His Leu Val Ser Phe Glu Gln Glu Ile
        275                 280                 285

Phe Asn Val Val Leu Lys Thr Val Ser Glu Ser Ala Thr Gln Pro Pro
    290                 295                 300

Thr Lys Val Tyr Asn Asn Asp Leu Thr Ala Ser Leu Met Val Ala Leu
305                 310                 315                 320

Asp Ser Asn Asn Thr Met Pro Phe Thr Pro Ala Ala Met Arg Ser Glu
                325                 330                 335

Thr Leu Gly Phe Tyr Pro Trp Lys Pro Thr Ile Pro Thr Pro Trp Arg
            340                 345                 350

Tyr Tyr Phe Gln Trp Asp Arg Thr Leu Ile Pro Ser His Thr Gly Thr
        355                 360                 365

Ser Gly Thr Pro Thr Asn Ile Tyr His Gly Thr Asp Pro Asp Asp Val
    370                 375                 380

Gln Phe Tyr Thr Ile Glu Asn Ser Val Pro Val His Leu Leu Arg Thr
385                 390                 395                 400

Gly Asp Glu Phe Ala Thr Gly Thr Phe Tyr Phe Asp Cys Lys Pro Cys
                405                 410                 415

Arg Leu Thr His Thr Trp Gln Thr Asn Arg Ala Leu Gly Leu Pro Pro
            420                 425                 430

Phe Leu Asn Ser Leu Pro Gln Ala Glu Gly Gly Thr Asn Phe Gly Tyr
        435                 440                 445

Ile Gly Val Gln Gln Asp Lys Arg Arg Gly Val Thr Gln Met Gly Asn
    450                 455                 460

Thr Asn Ile Ile Thr Glu Ala Thr Ile Met Arg Pro Ala Glu Val Gly
465                 470                 475                 480

Tyr Ser Ala Pro Tyr Tyr Ser Phe Glu Ala Ser Thr Gln Gly Pro Phe
                485                 490                 495

Lys Thr Pro Ile Ala Ala Gly Arg Gly Gly Ala Gln Thr Asp Glu Asn
            500                 505                 510

Gln Ala Ala Asp Gly Asp Pro Arg Tyr Ala Phe Gly Arg Gln His Gly
        515                 520                 525

Gln Lys Thr Thr Thr Thr Gly Glu Thr Pro Glu Arg Phe Thr Tyr Ile
    530                 535                 540

Ala His Gln Asp Thr Gly Arg Tyr Pro Glu Gly Asp Trp Ile Gln Asn
545                 550                 555                 560

Ile Asn Phe Asn Leu Pro Val Thr Asn Asp Asn Val Leu Leu Pro Thr
                565                 570                 575

Asp Pro Ile Gly Gly Lys Ala Gly Ile Asn Tyr Thr Asn Ile Phe Asn
            580                 585                 590

Thr Tyr Gly Pro Leu Thr Ala Leu Asn Asn Val Pro Pro Val Tyr Pro
```

-continued

```
                    595                 600                 605
Asn Gly Gln Ile Trp Asp Lys Glu Phe Asp Thr Asp Leu Lys Pro Arg
    610                 615                 620

Leu His Val Asn Ala Pro Phe Val Cys Gln Asn Asn Cys Pro Gly Gln
625                 630                 635                 640

Leu Phe Val Lys Val Ala Pro Asn Leu Thr Asn Glu Tyr Asp Pro Asp
                645                 650                 655

Ala Ser Ala Asn Met Ser Arg Ile Val Thr Tyr Ser Asp Phe Trp Trp
                660                 665                 670

Lys Gly Lys Leu Val Phe Lys Ala Lys Leu Arg Ala Ser His Thr Trp
                675                 680                 685

Asn Pro Ile Gln Gln Met Ser Ile Asn Val Asp Asn Gln Phe Asn Tyr
            690                 695                 700

Val Pro Ser Asn Ile Gly Gly Met Lys Ile Val Tyr Glu Lys Ser Gln
705                 710                 715                 720

Leu Ala Pro Arg Lys Leu Tyr
                725
```

<210> SEQ ID NO 76
<211> LENGTH: 727
<212> TYPE: PRT
<213> ORGANISM: Canine parvovirus 2b

<400> SEQUENCE: 76

```
Met Ala Pro Pro Ala Lys Arg Ala Arg Arg Gly Leu Val Pro Pro Gly
1               5                   10                  15

Tyr

-continued

```
Leu Asp Asp Thr His Ala Gln Ile Val Thr Pro Trp Ser Leu Val Asp
            245                 250                 255

Ala Asn Ala Trp Gly Val Trp Phe Asn Pro Gly Asp Trp Gln Leu Ile
        260                 265                 270

Val Asn Thr Met Ser Glu Leu His Leu Val Ser Phe Glu Gln Glu Ile
    275                 280                 285

Phe Asn Val Val Leu Lys Thr Val Ser Glu Ser Ala Thr Gln Pro Pro
290                 295                 300

Thr Lys Val Tyr Asn Asn Asp Leu Thr Ala Ser Leu Met Val Ala Leu
305                 310                 315                 320

Asp Ser Asn Asn Thr Met Pro Phe Thr Pro Ala Ala Met Arg Ser Glu
                325                 330                 335

Thr Leu Gly Phe Tyr Pro Trp Lys Pro Thr Ile Pro Thr Pro Trp Arg
            340                 345                 350

Tyr Tyr Phe Gln Trp Asp Arg Thr Leu Ile Pro Ser His Thr Gly Thr
        355                 360                 365

Ser Gly Thr Pro Thr Asn Ile Tyr His Gly Thr Asp Pro Asp Asp Val
    370                 375                 380

Gln Phe Tyr Thr Ile Glu Asn Ser Val Pro Val His Leu Leu Arg Thr
385                 390                 395                 400

Gly Asp Glu Phe Ala Thr Gly Thr Phe Tyr Phe Asp Cys Lys Pro Cys
                405                 410                 415

Arg Leu Thr His Thr Trp Gln Thr Asn Arg Ala Leu Gly Leu Pro Pro
            420                 425                 430

Phe Leu Asn Ser Leu Pro Gln Ala Glu Gly Gly Thr Asn Phe Gly Tyr
        435                 440                 445

Ile Gly Val Gln Gln Asp Lys Arg Arg Gly Val Thr Gln Met Gly Asn
    450                 455                 460

Thr Asn Ile Ile Thr Glu Ala Thr Ile Met Arg Pro Ala Glu Val Gly
465                 470                 475                 480

Tyr Ser Ala Pro Tyr Tyr Ser Phe Glu Ala Ser Thr Gln Gly Pro Phe
                485                 490                 495

Lys Thr Pro Ile Ala Ala Gly Arg Gly Gly Ala Gln Thr Asp Glu Asn
            500                 505                 510

Gln Ala Ala Asp Gly Asp Pro Arg Tyr Ala Phe Gly Arg Gln His Gly
        515                 520                 525

Gln Lys Thr Thr Thr Thr Gly Glu Thr Pro Glu Arg Phe Thr Tyr Ile
    530                 535                 540

Ala His Gln Asp Thr Gly Arg Tyr Pro Glu Gly Asp Trp Ile Gln Asn
545                 550                 555                 560

Ile Asn Phe Asn Leu Pro Val Thr Asp Asn Val Leu Leu Pro Thr
                565                 570                 575

Asp Pro Ile Gly Gly Lys Ala Gly Ile Asn Tyr Thr Asn Ile Phe Asn
            580                 585                 590

Thr Tyr Gly Pro Leu Thr Ala Leu Asn Asn Val Pro Pro Val Tyr Pro
        595                 600                 605

Asn Gly Gln Ile Trp Asp Lys Glu Phe Asp Thr Asp Leu Lys Pro Arg
    610                 615                 620

Leu His Val Asn Ala Pro Phe Val Cys Gln Asn Asn Cys Pro Gly Gln
625                 630                 635                 640

Leu Phe Val Lys Val Ala Pro Asn Leu Thr Asn Glu Tyr Asp Pro Asp
                645                 650                 655

Ala Ser Ala Asn Met Ser Arg Ile Val Thr Tyr Ser Asp Phe Trp Trp
```

```
                660                 665                 670
Lys Gly Lys Leu Val Phe Lys Ala Lys Leu Arg Ala Ser His Thr Trp
            675                 680                 685

Asn Pro Ile Gln Gln Met Ser Ile Asn Val Asp Asn Gln Phe Asn Tyr
        690                 695                 700

Val Pro Ser Asn Ile Gly Gly Met Lys Ile Val Tyr Glu Lys Ser Gln
705                 710                 715                 720

Leu Ala Pro Arg Lys Leu Tyr
                725

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Gln Gln Ser Gly Gly Gly Leu Val Gln Ala Gly Gly
1               5                   10                  15

Ser Leu Arg Leu Ser Cys Ala Ala Ser Gly Leu Thr Phe Gly Ser Pro
            20                  25                  30

Ala Met Ala Trp Tyr Arg Gln Ala Pro Gly Lys Glu Arg Glu Trp Val
        35                  40                  45

Ala Thr Ile Ser Arg Gly Gly Ser Thr Tyr Tyr Ala Asp Ser Val Lys
    50                  55                  60

Gly Arg Phe Thr Ile Ser Arg Asp Asn Ala Lys Asn Thr Ser Tyr Leu
65                  70                  75                  80

Gln Met Asn Ser Leu Lys Pro Glu Glu Thr Ala Val Tyr Tyr Cys Ala
                85                  90                  95

Ala Gly Leu Ser Ser Met Arg Tyr Asp Tyr Trp Gly Gln Gly Thr Gln
            100                 105                 110

Val Thr Val Ser Ser
        115

<210> SEQ ID NO 78
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Gln Gln Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Tyr Val
        35                  40                  45

Ala Gly Ile Asn Arg Phe Gly Gly Thr Tyr Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ser Arg Ile Leu Gly Leu Ser Thr Ala Arg Glu Asp Tyr Asn Tyr
```

```
Trp Gly Gln Gly Thr Gln Val Thr Val Ser Ser
        115                 120
```

<210> SEQ ID NO 79
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Gln Val Gln Leu Gln Glu Ser Gly Gly Gly Leu Val Gln Thr Gly Ala
1               5                   10                  15

Ser Leu Arg Leu Ser Cys Ala Val Ser Gly Arg Arg Ile Thr Asp Tyr
            20                  25                  30

Ile Ile Gly Trp Phe Arg Gln Ala Pro Gly Lys Glu Arg Glu Phe Val
        35                  40                  45

Gly Gln Ile Ser Arg Ser Ala Asn Ser Ile Ile Ala Asn Ser Val Lys
    50                  55                  60

Gly Arg Phe Thr Ile Ser Arg Asp Asn Ala Asn Asn Thr Val Ser Leu
65                  70                  75                  80

Gln Met Asn Ser Leu Lys Pro Asp Asp Thr Ala Val Tyr Leu Cys Gly
                85                  90                  95

Ala Ser Ser Ser Ile Gly Val Trp Thr Thr Ser Gln Tyr Tyr Asp Tyr
            100                 105                 110

Trp Gly Gln Gly Thr Arg Val Thr Val Ser Ser
        115                 120
```

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Gly Leu Thr Phe Gly Ser Pro Ala Met
1               5
```

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Gly Arg Thr Phe Ser Ser Tyr Ala Met
1               5
```

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Arg Arg Ile Thr Asp Tyr Ile Ile
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Ser Arg Gly Gly Ser Thr
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Asn Arg Phe Gly Gly Thr
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ile Ser Arg Ser Ala Asn Ser
1               5

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ala Gly Leu Ser Ser Met Arg Tyr Asp Tyr
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Ala Ser Arg Ile Leu Gly Leu Ser Thr Ala Arg Glu Asp Tyr Asn
1               5                   10                  15

Tyr

<210> SEQ ID NO 88
<211> LENGTH: 17
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 88

```
Gly Ala Ser Ser Ser Ile Gly Val Trp Thr Thr Ser Gln Tyr Tyr Asp
1               5                   10                  15

Tyr
```

<210> SEQ ID NO 89
<211> LENGTH: 727
<212> TYPE: PRT
<213> ORGANISM: Mink enteritis virus

<400> SEQUENCE: 89

```
Met Ala Pro Pro Ala Lys Arg Ala Arg Arg Gly Leu Val Pro Pro Gly
1               5                   10                  15

Tyr Lys Tyr Leu Gly Pro Gly Asn Ser Leu Asp Gln Gly Glu Pro Thr
            20                  25                  30

Asn Pro Ser Asp Ala Ala Ala Lys Glu His Asp Glu Ala Tyr Ala Ala
        35                  40                  45

Tyr Leu Arg Ser Gly Lys Asn Pro Tyr Leu Tyr Phe Ser Pro Ala Asp
    50                  55                  60

Gln Arg Phe Ile Asp Gln Thr Lys Asp Ala Lys Asp Trp Gly Gly Lys
65                  70                  75                  80

Ile Gly His Tyr Phe Phe Arg Asp Lys Lys Ala Ile Ala Pro Val Leu
                85                  90                  95

Ser Asp Thr Pro Asp His Pro Ser Thr Ser Arg Pro Ala Lys Pro Ser
            100                 105                 110

Lys Arg Cys Lys Pro Pro Pro His Ile Phe Ile Asn Leu Ala Lys Lys
        115                 120                 125

Lys Asn Ala Gly Ala Ala Gln Val Lys Arg Asp Asn Leu Ala Pro Met
    130                 135                 140

Ser Asp Gly Ala Val Gln Pro Asp Gly Gly Gln Pro Ala Val Arg Asn
145                 150                 155                 160

Glu Arg Ala Thr Gly Ser Gly Asn Gly Ser Gly Gly Gly Gly Gly Gly
                165                 170                 175

Gly Ser Gly Gly Val Gly Ile Ser Thr Gly Thr Phe Asn Asn Gln Thr
            180                 185                 190

Glu Phe Lys Phe Leu Glu Asn Gly Trp Val Glu Ile Thr Ala Asn Ser
        195                 200                 205

Ser Arg Leu Val His Leu Asn Met Pro Glu Ser Glu Asn Tyr Lys Arg
    210                 215                 220

Val Val Val Asn Asn Met Asp Lys Thr Ala Val Lys Gly Asn Met Ala
225                 230                 235                 240

Leu Asp Asp Thr His Val Gln Ile Val Thr Pro Trp Ser Leu Val Asp
                245                 250                 255

Ala Asn Ala Trp Gly Val Trp Phe Asn Pro Gly Asp Trp Gln Leu Ile
            260                 265                 270

Val Asn Thr Met Ser Glu Leu His Leu Val Ser Phe Glu Gln Glu Ile
        275                 280                 285

Phe Asn Val Val Leu Lys Thr Val Ser Glu Ser Ala Thr Gln Pro Pro
    290                 295                 300

Thr Lys Val Tyr Asn Asn Asp Leu Thr Ala Ser Leu Met Val Ala Leu
305                 310                 315                 320
```

```
Asp Ser Asn Asn Thr Met Pro Phe Thr Pro Ala Ala Met Arg Ser Glu
                325                 330                 335

Thr Leu Gly Phe Tyr Pro Trp Lys Pro Thr Ile Pro Thr Pro Trp Arg
            340                 345                 350

Tyr Tyr Phe Gln Trp Asp Arg Thr Leu Ile Pro Ser His Thr Gly Thr
        355                 360                 365

Ser Gly Thr Pro Thr Asn Ile Tyr His Gly Thr Asp Pro Asp Asp Val
    370                 375                 380

Gln Phe Tyr Thr Ile Glu Asn Ser Val Pro Val His Leu Leu Arg Thr
385                 390                 395                 400

Gly Asp Glu Phe Ala Thr Gly Thr Phe Phe Asp Cys Lys Pro Cys
                405                 410                 415

Arg Leu Thr His Thr Trp Gln Thr Asn Arg Ala Leu Gly Leu Pro Pro
                420                 425                 430

Phe Leu Asn Ser Leu Pro Gln Ser Glu Gly Ala Thr Asn Phe Gly Asp
                435                 440                 445

Ile Gly Val Gln Gln Asp Lys Arg Arg Gly Val Thr Gln Met Gly Asn
            450                 455                 460

Thr Asp Tyr Ile Thr Glu Ala Thr Ile Met Arg Pro Ala Glu Val Gly
465                 470                 475                 480

Tyr Ser Ala Pro Tyr Tyr Ser Phe Glu Ala Ser Thr Gln Gly Pro Phe
                485                 490                 495

Lys Thr Pro Ile Ala Ala Gly Arg Gly Gly Ala Gln Thr Asp Glu Asn
                500                 505                 510

Gln Ala Ala Asp Gly Asp Pro Arg Tyr Ala Phe Gly Arg Gln His Gly
            515                 520                 525

Gln Lys Thr Thr Thr Thr Gly Glu Thr Pro Glu Arg Phe Thr Tyr Ile
    530                 535                 540

Ala His Gln Asp Thr Gly Arg Tyr Pro Glu Gly Asp Trp Ile Gln Asn
545                 550                 555                 560

Ile Asn Phe Asn Leu Pro Val Thr Asn Asp Asn Val Leu Leu Pro Thr
                565                 570                 575

Asp Pro Ile Gly Gly Lys Thr Gly Ile Asn Tyr Thr Asn Ile Phe Asn
                580                 585                 590

Thr Tyr Gly Pro Leu Thr Ala Leu Asn Asn Val Pro Pro Val Tyr Pro
            595                 600                 605

Asn Gly Gln Ile Trp Asp Lys Glu Phe Asp Thr Asp Leu Lys Pro Arg
    610                 615                 620

Leu His Val Asn Ala Pro Phe Val Cys His Asn Asn Cys Pro Gly Gln
625                 630                 635                 640

Leu Phe Val Lys Val Ala Pro Asn Leu Thr Asn Glu Tyr Asp Pro Asp
                645                 650                 655

Ala Ser Ala Asn Met Ser Arg Ile Val Thr Tyr Ser Asp Phe Trp Trp
                660                 665                 670

Lys Gly Lys Leu Val Phe Lys Ala Lys Leu Arg Ala Ser His Thr Trp
            675                 680                 685

Asn Pro Ile Gln Gln Met Ser Ile Asn Val Asp Asn Gln Phe Asn Tyr
            690                 695                 700

Leu Pro Asn Asn Ile Gly Ala Met Lys Ile Val Tyr Glu Lys Ser Gln
705                 710                 715                 720

Leu Ala Pro Arg Lys Leu Tyr
                725
```

<210> SEQ ID NO 90
<211> LENGTH: 729
<212> TYPE: PRT
<213> ORGANISM: Ungulate protoparvovirus 1

<400> SEQUENCE: 90

Met Ala Pro Pro Ala Lys Arg Ala Arg Gly Leu Thr Leu Pro Gly Tyr
1               5                   10                  15

Lys Tyr Leu Gly Pro Gly Asn Ser Leu Asp Gln Gly Glu Pro Thr Asn
            20                  25                  30

Pro Ser Asp Ala Ala Ala Lys Glu His Asp Glu Ala Tyr Asp Lys Tyr
        35                  40                  45

Ile Lys Ser Gly Lys Asn Pro Tyr Phe Tyr Phe Ser Ala Ala Asp Glu
50                  55                  60

Lys Phe Ile Lys Glu Thr Glu His Ala Lys Asp Tyr Gly Gly Lys Ile
65                  70                  75                  80

Gly His Tyr Phe Phe Arg Ala Lys Arg Ala Phe Ala Pro Lys Leu Ser
                85                  90                  95

Glu Thr Asp Ser Pro Thr Thr Ser Gln Gln Pro Glu Val Arg Arg Ser
            100                 105                 110

Pro Arg Lys His Pro Gly Ser Lys Pro Gly Lys Arg Pro Ala Pro
        115                 120                 125

Arg His Ile Phe Ile Asn Leu Ala Lys Lys Ala Lys Gly Thr Ser
130                 135                 140

Asn Thr Asn Ser Asn Ser Met Ser Glu Asn Val Glu Gln His Asn Pro
145                 150                 155                 160

Ile Asn Ala Gly Thr Glu Leu Ser Ala Thr Gly Asn Glu Ser Gly Gly
                165                 170                 175

Gly Gly Gly Gly Gly Gly Arg Gly Ala Gly Val Gly Val Ser
            180                 185                 190

Thr Gly Ser Phe Asn Asn Gln Thr Glu Phe Gln Tyr Leu Gly Glu Gly
            195                 200                 205

Leu Val Arg Ile Thr Ala His Ala Ser Arg Leu Ile His Leu Asn Met
210                 215                 220

Pro Glu His Glu Thr Tyr Lys Arg Ile His Val Leu Asn Ser Glu Ser
225                 230                 235                 240

Gly Val Ala Gly Gln Met Val Gln Asp Asp Ala His Thr Gln Met Val
                245                 250                 255

Thr Pro Trp Ser Leu Ile Asp Ala Asn Ala Trp Gly Val Trp Phe Asn
            260                 265                 270

Pro Ala Asp Trp Gln Leu Ile Ser Asn Asn Met Thr Glu Ile Asn Leu
        275                 280                 285

Val Ser Phe Glu Gln Glu Ile Phe Asn Val Val Leu Lys Thr Ile Thr
290                 295                 300

Glu Ser Ala Thr Ser Pro Pro Thr Lys Ile Tyr Asn Asn Asp Leu Thr
305                 310                 315                 320

Ala Ser Leu Met Val Ala Leu Asp Thr Asn Asn Thr Leu Pro Tyr Thr
                325                 330                 335

Pro Ala Ala Pro Arg Ser Glu Thr Leu Gly Phe Tyr Pro Trp Leu Pro
            340                 345                 350

Thr Lys Pro Thr Gln Tyr Arg Tyr Tyr Leu Ser Cys Thr Arg Asn Leu
        355                 360                 365

Asn Pro Pro Thr Tyr Thr Gly Gln Ser Glu Gln Ile Thr Asp Ser Ile
370                 375                 380

Gln Thr Gly Leu His Ser Asp Ile Met Phe Tyr Thr Ile Glu Asn Ala
385                 390                 395                 400

Val Pro Ile His Leu Leu Arg Thr Gly Asp Glu Phe Ser Thr Gly Ile
            405                 410                 415

Tyr His Phe Asp Thr Lys Pro Leu Lys Leu Thr His Ser Trp Gln Thr
        420                 425                 430

Asn Arg Ser Leu Gly Leu Pro Pro Lys Leu Leu Thr Glu Pro Thr Thr
    435                 440                 445

Glu Gly Asp Gln His Pro Gly Thr Leu Pro Ala Ala Asn Thr Arg Lys
450                 455                 460

Gly Tyr His Gln Thr Ile Asn Asn Ser Tyr Thr Glu Ala Thr Ala Ile
465                 470                 475                 480

Arg Pro Ala Gln Val Gly Tyr Asn Thr Pro Tyr Met Asn Phe Glu Tyr
            485                 490                 495

Ser Asn Gly Gly Pro Phe Leu Thr Pro Ile Val Pro Thr Ala Asp Thr
        500                 505                 510

Gln Tyr Asn Asp Asp Glu Pro Asn Gly Ala Ile Arg Phe Thr Met Gly
    515                 520                 525

Tyr Gln His Gly Gln Leu Thr Thr Ser Ser Gln Glu Leu Glu Arg Tyr
530                 535                 540

Thr Phe Asn Pro Gln Ser Lys Cys Gly Arg Ala Pro Lys Gln Gln Phe
545                 550                 555                 560

Asn Gln Gln Ser Pro Leu Asn Leu Gln Asn Thr Asn Asn Gly Thr Leu
            565                 570                 575

Leu Pro Ser Asp Pro Ile Gly Gly Lys Thr Asn Met His Phe Met Asn
        580                 585                 590

Thr Leu Asn Thr Tyr Gly Pro Leu Thr Ala Leu Asn Asn Thr Ala Pro
    595                 600                 605

Val Phe Pro Asn Gly Gln Ile Trp Asp Lys Glu Leu Asp Thr Asp Leu
610                 615                 620

Lys Pro Arg Leu His Val Thr Ala Pro Phe Val Cys Lys Asn Asn Pro
625                 630                 635                 640

Pro Gly Gln Leu Phe Val Lys Ile Ala Pro Asn Leu Thr Asp Asp Phe
            645                 650                 655

Asn Ala Asp Ser Pro Gln Gln Pro Arg Ile Ile Thr Tyr Ser Asn Phe
        660                 665                 670

Trp Trp Lys Gly Thr Leu Thr Phe Thr Ala Lys Met Arg Ser Ser Asn
    675                 680                 685

Met Trp Asn Pro Ile Gln Gln His Thr Thr Thr Ala Glu Asn Ile Gly
690                 695                 700

Asn Tyr Ile Pro Thr Asn Ile Gly Gly Ile Lys Met Phe Pro Glu Tyr
705                 710                 715                 720

Ser Gln Leu Ile Pro Arg Lys Leu Tyr
            725

<210> SEQ ID NO 91
<211> LENGTH: 729
<212> TYPE: PRT
<213> ORGANISM: Mouse parvovirus 1

<400> SEQUENCE: 91

Met Ala Pro Pro Ala Lys Arg Ala Lys Arg Gly Trp Val Pro Pro Gly
1               5                   10                  15

Tyr Lys Tyr Leu Gly Pro Gly Asn Ser Leu Asp Gln Gly Glu Pro Thr

```
                     20                  25                  30
Asn Pro Ser Asp Ala Ala Lys Glu His Asp Glu Ala Tyr Asp Lys
             35                  40                  45

Tyr Ile Lys Ser Gly Lys Asn Pro Tyr Leu Tyr Phe Ser Ala Ala Asp
         50                  55                  60

Gln Arg Phe Ile Asp Gln Thr Lys Asp Ala Lys Asp Trp Gly Gly Lys
 65                  70                  75                  80

Val Gly His Tyr Phe Phe Arg Thr Lys Arg Ala Phe Ala Pro Arg Leu
                 85                  90                  95

Ala Ser Ser Ser Glu Pro Gly Thr Ser Gly Val Ser Ile Ala Gly Lys
                100                 105                 110

Arg Thr Lys Pro Pro Ala His Ile Phe Ile Asn Gln Ala Arg Ala Lys
             115                 120                 125

Lys Lys Arg Ala Ser Leu Ala Ala Gln Gln Arg Thr Gln Thr Met Ser
         130                 135                 140

Asp Gly Ala Glu Gln Pro Asp Ser Gly Ser Ala Val Gln Ser Ala Ala
145                 150                 155                 160

Arg Val Glu Arg Ala Ala Asp Gly Pro Gly Ser Gly Gly Gly Gly
                165                 170                 175

Ser Gly Gly Gly Val Gly Val Ser Thr Gly Ser Tyr Asp Asn Gln
                180                 185                 190

Thr His Tyr Arg Phe Leu Ser Asp Gly Trp Val Glu Ile Thr Ala Tyr
             195                 200                 205

Ser Thr Arg Met Val His Leu Asn Met Pro Lys Ser Glu Asn Tyr Cys
         210                 215                 220

Arg Val Arg Val His Asn Thr Asn Asp Thr Arg Thr Ala Gly Asn Met
225                 230                 235                 240

Ala Lys Asp Asp Ala His Glu Gln Ile Trp Thr Pro Trp Ser Leu Ile
                245                 250                 255

Asp Ser Asn Ala Trp Gly Val Trp Phe Gln Pro Ser Asp Trp Gln Phe
                260                 265                 270

Ile Cys Asn Asn Met Ser His Val Asn Leu His Ser Leu Asp Gln Glu
             275                 280                 285

Leu Phe Asn Val Val Ile Lys Thr Val Thr Glu Gln Asn Thr Gly Ala
         290                 295                 300

Glu Ala Val Lys Ile Tyr Asn Asn Asp Leu Thr Ala Ser Met Met Val
305                 310                 315                 320

Ala Leu Asp Ser Asn Asn Ile Leu Pro Tyr Thr Pro Ala Thr Asp Asn
                325                 330                 335

Gln Glu Thr Leu Gly Phe Tyr Pro Trp Lys Pro Thr Met Pro Ser Pro
                340                 345                 350

Tyr Arg Tyr Tyr Phe Asn Cys Asp Arg Ser Leu Ser Val Thr Tyr Thr
             355                 360                 365

Asp Gln Thr Gly Ser Ile Val Asp Thr Met Ala Asn Ala Ser Gly Leu
         370                 375                 380

Ser Ser Gln Phe Phe Thr Ile Glu Asn Thr Gln Arg Ile Gln Leu Leu
385                 390                 395                 400

Arg Thr Gly Asp Glu Phe Ala Thr Gly Thr Tyr Tyr Phe Glu Thr Glu
                405                 410                 415
```

```
Pro Ile Lys Leu Ser His Thr Trp Gln Ser Asn Arg Gln Leu Gly Gln
            420                 425                 430

Pro Pro Gln Ile Thr Asp Leu Pro Thr Ala Asp Asn Glu Asn Ala Thr
            435                 440                 445

Leu Val Thr Arg Gly Asp Arg Ser Gly Ile Thr Gln Ile Ser Gly Ser
        450                 455                 460

Asn Asp Val Thr Glu Ala Thr Arg Val Arg Pro Ala Gln Val Gly Phe
465                 470                 475                 480

Cys Gln Pro His Asp Asn Phe Glu Thr Ser Arg Ala Gly Pro Phe Lys
            485                 490                 495

Val Pro Val Pro Ala Asn Val Thr Gln Gly Asn Glu His Asp Ala
            500                 505                 510

Asn Gly Ser Leu Arg Tyr Thr Tyr Asp Lys Gln His Gly Gln Asp Trp
            515                 520                 525

Gly Ser Asn Asn Ser Lys Glu Arg Phe Thr Trp Asp Ala Ile Ser Tyr
            530                 535                 540

Asp Ser Gly Arg Trp Ala Asp Arg Cys Phe Ile Asn Ala Thr Pro Phe
545                 550                 555                 560

Thr Ser Pro Pro Ala Leu Asn Asn Ile Leu Thr Asn Ser Asp Pro Ile
            565                 570                 575

Gly Asn Lys Thr Ala Ile His Tyr Gln Asn Val Phe Asn Ser Tyr Gly
            580                 585                 590

Pro Leu Thr Ala Phe Pro His Pro Ala Pro Ile Tyr Pro Gln Gly Gln
            595                 600                 605

Ile Trp Asp Lys Glu Leu Asp Leu Glu His Lys Pro Arg Leu His Ala
            610                 615                 620

Gln Ala Pro Phe Val Cys Lys Asn Asn Ala Pro Gly Gln Leu Leu Val
625                 630                 635                 640

Arg Leu Ala Pro Asn Leu Thr Asp Gln Tyr Asp Pro Asn Ser Ser Thr
            645                 650                 655

Leu Ser Arg Ile Val Thr Tyr Gly Thr Phe Phe Trp Lys Gly Lys Leu
            660                 665                 670

Thr Leu Lys Ala Lys Leu Arg Pro Asn Ala Thr Trp Asn Pro Val Tyr
            675                 680                 685

Gln Val Ser Ala Gln Tyr Gln Asn Glu Asn Glu Tyr Met Ser Ile His
            690                 695                 700

Lys Trp Leu Pro Thr Ala Thr Gly Asn Met Gln Ser Ile Pro Leu Leu
705                 710                 715                 720

Ser Arg Pro Val Ala Arg Asn Thr Tyr
            725

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 92

His His His His His His
1               5
```

ANTIBODIES AGAINST DISEASE CAUSING AGENTS OF CANINES AND FELINES AND USES THEREOF

CROSS-REFERENCE TO RELATED APPLICATIONS

This application claims the benefit of U.S. Provisional Application No. 62/760,765, filed Nov. 13, 2018, which application is incorporated herein by reference. Priority is claimed pursuant to 35 U.S.C. § 119. The above noted patent application is incorporated by reference as if set forth fully herein.

ELECTRONIC SEQUENCE LISTING

The instant application hereby incorporates by reference in its entirety, the material of the electronic Sequence Listing which has been submitted electronically in ASCII format. Said ASCII copy of the material in the electronic Sequence Listing is submitted as a text (.txt) file entitled "105926-033—Updated Sequence listing.txt", created on Jan. 25, 2024, which has a file size of 81042 bytes, and is herein incorporated by reference in its entirety.

FIELD OF THE INVENTION

This invention relates to methods and compositions for the control of microorganisms associated with infections in canines and uses thereof.

BACKGROUND OF THE INVENTION

Domestic dogs and cats, along with wild canine and feline species, can suffer from severe infections caused by viruses of the Parvoviridae family Amongst infectious diseases, canine parvovirus is one of the leading causes of morbidity and mortality in dogs. Infection results in fever, vomiting, dehydration, and diarrhea. Untreated, most dogs will die from the infection. Current therapies rely on high-cost supportive therapies, such as blood transfusions, IV feeding, and 24-hour care at veterinary hospitals. Canine parvovirus infections are very costly to dog owners, both financially and emotionally. Furthermore, these infections result in lost productivity when individuals stay home from work to care for their dogs. These infections can result in up to 90% mortality in puppies and 10% mortality in adult dogs (Nandi & Kumar, 2010).

The situation is similar in domestic cats, particularly kittens. Feline parvovirus (also known as feline panleukopenia virus) infections results in symptoms that include anemia, fever, vomiting, diarrhea, and decreased white blood cell counts (panleukopenia). Current treatments are high-cost supportive therapies. These infections can result in up to 90% mortality in the acute form of the disease (Stuetzer & Hartmann, 2014).

There is a need for the development of pathogen-specific molecules that inhibit these infections or the association of these pathogens with their hosts.

SUMMARY OF THE INVENTION

With reference to the definitions set out below, described herein are polypeptides comprising heavy chain variable region fragments (VHHs) whose intended use includes but is not limited to the following applications in animal health or an unrelated field: diagnostics, in vitro assays, feed, therapeutics, substrate identification, nutritional supplementation, bioscientific and medical research, and companion diagnostics. Also described herein are polypeptides comprising VHHs that bind and decrease the virulence of disease-causing agents in canines or felines. Further to these descriptions, set out below are the uses of polypeptides that comprise VHHs in methods of reducing transmission and severity of disease in host animals, including their use as an ingredient in a product. Further described are the means to produce, characterise, refine and modify VHHs for this purpose.

One aspect of the disclosure includes polypeptide capable of preventing red blood cell hemagglutination by canine parvovirus type 2C capsid at a concentration lower than 100 nM. Another aspect of the disclosure includes a polypeptide capable of preventing red blood cell hemagglutination by canine parvovirus type 2C capsid at a concentration lower than 1 µM. Another aspect of the disclosure includes a polypeptide capable of reducing invasion of MDCK cells by canine parvovirus by >50% at 5 µM. Another aspect of the disclosure includes a polypeptide comprising at least one variable region fragment of a heavy chain antibody ($V_HH$), wherein the at least one $V_HH$ specifically binds a parvovirus. In some embodiments, such polypeptide comprises a plurality of $V_HHs$. In some embodiments, the polypeptide comprises at least three $V_HHs$. In some embodiments, any one of the plurality of $V_HHs$ is identical to another $V_HH$ of the plurality of $V_HHs$. Alternatively and/or additionally, the plurality of $V_HHs$ are covalently coupled to one another by a linker, the linker comprising one or more amino acids.

In some embodiments, the variable region fragment of the heavy chain antibody comprises an amino acid sequence at least 80%, 90%, 95%, 97%, 98%, 99%, or 100% identical to any one of SEQ ID NOs: 1 to 18 or 77 to 79. Alternatively and/or additionally, the variable region fragment of the heavy chain antibody comprises a complementarity determining region 1 (CDR1) as set forth in any one of SEQ ID NOs: 19 to 35 or 80 to 82, a complementarity determining region 2 (CDR2) as set forth in any one of SEQ ID NOs: 37 to 53 or 83 to 85, and a complementarity determining region 3 (CDR3) as set forth in any one of SEQ ID NOs: 55 to 72 or 86 to 88.

Another aspect of the disclosure includes a polypeptide complex that comprises a first component polypeptide and a second component polypeptide, wherein the first component polypeptide and the second component polypeptide are not covalently linked together and are coupled together by a protein-protein interaction, a small molecule-protein interaction, or a small molecule-small molecule interaction, wherein each of the first and the second component polypeptides comprise a $V_HH$ which specifically binds a pathogen.

In some embodiments, with respect to the polypeptide or the polypeptide complex as described herein, the pathogen is a parvovirus. In some embodiments, respect to the polypeptide or the polypeptide complex as described herein, the parvovirus is from the Parvovirinae subfamily. Alternatively and/or additionally, the parvovirus is from the Densovirinae subfamily. Alternatively and/or additionally, the parvovirus is from the *Protoparvovirus* genus. Alternatively and/or additionally, the parvovirus comprises a canine parvovirus. Alternatively and/or additionally, the canine parvovirus comprises a canine parvovirus type 2. Alternatively and/or additionally, the canine parvovirus is canine parvovirus type 2, canine parvovirus type 2a, canine parvovirus type 2b, or canine parvovirus type 2c.

In some embodiments, the $V_HH$ specifically binds a canine parvovirus virulence factor. Alternatively and/or additionally, the $V_HH$ specifically binds an antigen or polypeptide at least 60%, 70%, 80%, 90%, 95%, 98%, 99%, or 100% identical to SEQ IDs NO: 73 or 75 or 76. Alternatively and/or additionally, the canine parvovirus virulence factor is an infectious canine parvovirus virus particle, a canine parvovirus virus-like particle, or a canine parvovirus capsid protein.

In some embodiments, the parvovirus comprises a feline parvovirus. Alternatively and/or additionally, the parvovirus is feline panleukopenia virus. Alternatively and/or additionally, the $V_HH$ specifically binds a feline parvovirus virulence factor. Alternatively and/or additionally, the $V_HH$ specifically binds an antigen or polypeptide having a sequence at least 60%, 70%, 80%, 90%, 95%, 98%, 99%, or 100% identical to SEQ ID NO: 74. Alternatively and/or additionally, the feline parvovirus virulence factor is an infectious feline parvovirus virus particle, a feline parvovirus virus-like particle, or a feline parvovirus capsid protein.

In some embodiments, the parvovirus comprises a mink parvovirus. Alternatively and/or additionally, the parvovirus is mink enteritis virus. Alternatively and/or additionally, the $V_HH$ specifically binds a mink parvovirus virulence factor. Optionally, the mink parvovirus virulence factor is an infectious mink parvovirus virus particle, a mink parvovirus virus-like particle, or a mink parvovirus capsid protein Where the parvovirus comprises a mink parvovirus, it is contemplated that the $V_HH$ specifically binds an antigen or polypeptide having a sequence at least 60%, 70%, 80%, 90%, 95%, 98%, 99%, or 100% identical to SEQ ID NO: 89.

In some embodiments, the parvovirus comprises a swine parvovirus. Alternatively and/or additionally, the parvovirus comprises a mouse parvovirus.

Another aspect of the disclosure includes a nucleic acid encoding the polypeptide or a polypeptide complex described herein. Another aspect of the disclosure includes a plurality of nucleic acids encoding the polypeptide complex described herein. Another aspect of the disclosure includes a vector comprising the nucleic acid encoding the polypeptide or a polypeptide complex or a plurality of nucleic acids encoding the polypeptide complex in any production system.

Another aspect of the disclosure includes a cell comprising the nucleic acid or the plurality of nucleic acids as described herein. In some embodiments, the cell is a yeast cell. Optionally, the yeast is of the genus *Pichia*. Alternatively and/or additionally, the yeast is of the genus *Saccharomyces*. In some embodiments, the cell is a bacterial cell. Optionally, the bacteria is of the genus *Escherichia*. Alternatively and/or additionally, the bacteria is a probiotic bacterium. Alternatively and/or additionally, the probiotic bacteria is selected from the group consisting of the genus *Bacillus*, the genus *Lactobacillus*, the genus *Bifidobacterium*.

In some embodiments, the polypeptide or the polypeptide complex described herein is synthesized in any de novo protein synthesis system. In some embodiments, the polypeptide or the polypeptide complex described herein further comprises meat, a meat by-product, bone meal, fish, fish meal, egg, egg by-product, a vitamin, vegetables, plant matter, plant extracts, an amino acid, a dye, an antibiotic, an antiviral, a hormone, an antimicrobial peptide, a steroid, a prebiotic, a probiotic, a bacteriophage, chitin, chitosan, B-1,3-glucan, vegetable extracts, peptone, krill, algae, B-cyclodextran, alginate, gum, tragacanth, pectin, gelatin, an additive spray, a toxin binder, a short chain fatty acid, a medium chain fatty acid, an omega-3 fatty acid, yeast, a yeast extract, a plant extract, sugar, a digestive enzyme, a digestive compound, an essential mineral, carnitine, glucosamine, an essential salt, fibre, a preservative, a stabilizer, a natural flavour, an artificial flavour, or water.

Another aspect of the disclosure includes a method of producing the polypeptide or the polypeptide complex described herein, comprising (a) incubating a cell in a medium suitable for secretion of the polypeptide from the cell; and (b) purifying the polypeptide from the medium.

Another aspect of the disclosure includes the polypeptide or the polypeptide complex described herein for use in reducing or preventing a canine-associated viral infection in a canine, or another animal species. Another aspect of the disclosure includes use of the polypeptide or the polypeptide complex described herein for reducing transmission or preventing transmission of a canine-associated virus from a canine species to another canine or another animal species. In some embodiments, the canine species comprises a domestic dog, wolf, coyote, fox, jackal, or dingo. Alternatively and/or additionally, the another animal species comprises a feline, mink, skunk or raccoon.

Another aspect of the disclosure includes the polypeptide or the polypeptide complex described herein for use in reducing or preventing a feline-associated viral infection in a feline, or another animal species. Another aspect of the disclosure includes use of the polypeptide or the polypeptide complex described herein for reducing transmission or preventing transmission of a feline-associated virus from a feline species to another feline or another animal species. In some embodiments, the feline species comprises a domestic cat, wild cat, leopard, tiger, jaguar, lion, serval, caracal, ocelot, margay, kodkod, oncilla, bobcat, lynx, cheetah, cougar, or jaguarundi. Alternatively and/or additionally, the another animal species comprises a canine, mink, skunk or raccoon.

Another aspect of the disclosure includes the polypeptide or the polypeptide complex described herein for use in reducing or preventing a mink-associated viral infection in a mink, or another animal species. Another aspect of the disclosure includes use of the polypeptide or the polypeptide complex described herein for reducing transmission or preventing transmission of a mink-associated virus from a mink species to another mink or another animal species.

In uses of above, in some embodiments, it is contemplated that the polypeptide is adapted for introduction to the alimentary canal orally or rectally, provided to the exterior surface (for example, as a spray or submersion), provided to the medium in which the animal dwells (including air based media), provided by injection, provided intravenously, provided via the respiratory system, provided via diffusion, provided via absorption by the endothelium or epithelium, or provided via a secondary organism selected from the group consisting of a yeast, bacterium, algae, bacteriophages, plants and insects to a host.

DEFINITIONS

In describing the present invention, the following terminology is used in accordance with the definitions below.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

Host

As referred to herein, "host", "host organism", "recipient animal", "host animal" and variations thereof refer to the intended recipient of the product when the product constitutes a feed or a therapeutic. In certain embodiments, the host is a vertebrate. In certain embodiments, the host is from the order Carnivora. In certain embodiments, the host is from the family Canidae. In certain embodiments, the host is a domestic dog, wolf, coyote, fox, jackal, or dingo. In certain embodiments, the host is a domestic dog. In certain embodiments, the host is from the family Felidae. In certain embodiments, the host is a domestic cat, a wild cat, leopard, tiger, jaguar, lion, serval, caracal, ocelot, margay, kodkod, oncilla, bobcat, lynx, cheetah, cougar, or jaguarundi. In certain embodiments, the host is a domestic cat. In certain embodiments, the vertebrate host is a non-canine and non-feline species. In certain embodiments, the non-canine and non-feline species is a mink, skunk or raccoon. In certain embodiments, the vertebrate host is a human, swine species, poultry species, ovine species, bovine species, horse, or mouse. In certain embodiments, the host is an invertebrate. In certain embodiments, the invertebrate is a shrimp species.

Pathogens

Figure 1:
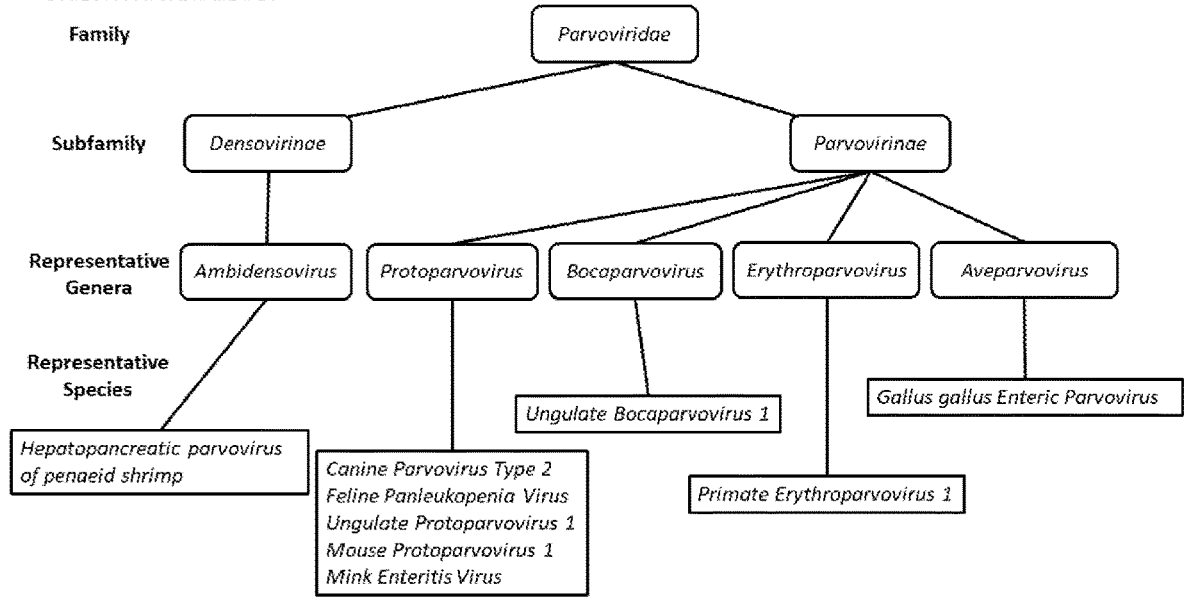
FIG. 1 illustrates the scientific classification of the Parvoviruses with representative genera and species that cause infections.

As referred to herein, "pathogen", "pathogenic", and variations thereof refer to virulent microorganisms, that can be associated with host organisms, that give rise to a symptom or set of symptoms in that organism that are not present in uninfected host organisms, including the reduction in ability to survive, thrive, or reproduce. Without limitation, pathogens encompass parasites, bacteria, viruses, prions, protists, fungi and algae. In certain embodiments, the pathogen is a virus belonging to the family Parvoviridae (FIG. 1). In certain embodiments, the pathogen is a virus belonging to the subfamily Parvovirinae. In certain embodiments, the pathogen is a virus belonging to the Protoparvovirus genera. In certain embodiments, the pathogen is canine parvovirus type 2. In certain embodiments, the pathogen is feline panleukopenia virus. In certain embodiments the pathogen is mink enteritis virus. In certain embodiments, the pathogen is ungulate protoparvovirus 1. In certain embodiments, the pathogen is mouse protoparvovirus 1. In certain embodiments, the pathogen is a virus belonging to the Bocaparvovirus genera. In certain embodiments, the pathogen is ungulate bocaparvovirus 1. In certain embodiments, the pathogen is a virus belonging to the *Erythroparvovirus* genera. In certain embodiments, the pathogen is primate erythroparvovirus 1. In certain embodiments, the pathogen is a virus belonging to the *Aveparvovirus* genera. In certain embodiments, the pathogen is *Gallus gallus* enteric parvovirus. In certain embodiments, the pathogen is a virus belonging to the subfamily Densovirinae. In certain embodiments, the pathogen is a virus belonging to the *Ambidensovirus* genera. In certain embodiments, the pathogen is hepatopancreatic parvovirus of penaeid shrimp.

"Virulence", "virulent" and variations thereof refer to a pathogen's ability to cause symptoms in a host organism. "Virulence factor" refers to nucleic acids, plasmids, genomic islands, genes, peptides, proteins, toxins, lipids, macromolecular machineries or complexes thereof that have a demonstrated or putative role in infection.

"Disease-causing agent" refers to a microorganism, pathogen or virulence factor with a demonstrated or putative role in infection.

Antibodies

Figure 2A:
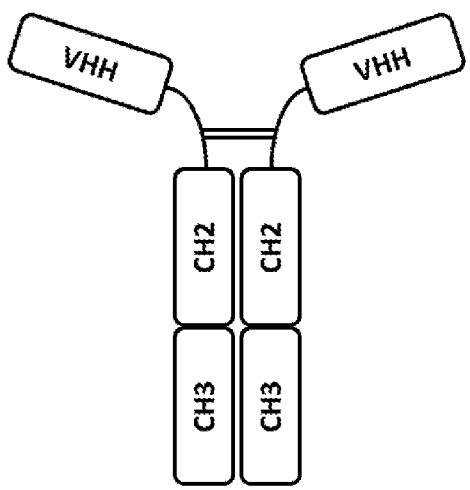
FIGS. 2A-B show a schematic of camelid heavy chain only antibodies and their relationship to $V_HH$ domains and complementarity determining regions (CDRs).
Figure 2B:
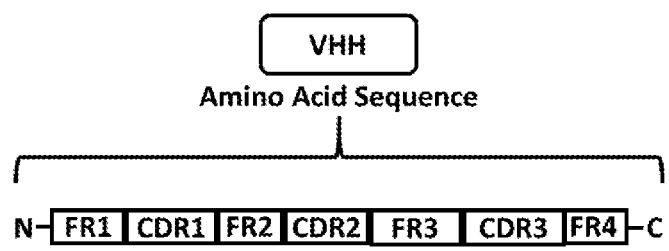

A schematic of camelid heavy chain only antibodies and their relationship to $V_HH$ domains and complementarity determining regions (CDRs) is shown in FIG. 2A A camelid heavy chain only antibody consists of two heavy chains linked by a disulphide bridge. Each heavy chain contains two constant immunoglobulin domains (CH2 and CH3) linked through a hinge region to a variable immunoglobulin domain ($V_HH$). (FIG. 2B) Each $V_HH$ domain contains an amino acid sequence of approximately 110-130 amino acids. The $V_HH$ domain consists of the following regions starting at the N-terminus (N): framework region 1 (FR1), complementarity-determining region 1 (CDR1), framework region 2 (FR2), complementarity-determining region 2 (CDR2), framework region 3 (FR3), complementarity-determining region 3 (CDR3), and framework region 4 (FR4). The domain ends at the C-terminus (C). The complementarity-determining regions are highly variable, determine antigen binding by the antibody, and are held together in a scaffold by the framework regions of the $V_HH$ domain. The framework regions consist of more conserved amino acid sequences; however, some variability exists in these regions.

As referred to herein "$V_HH$" refers to an antibody or antibody fragment comprising a single heavy chain variable region which may be derived from natural or synthetic sources. NBXs referred to herein are an example of a $V_HH$. In a certain aspect a $V_HH$ may lack a portion of a heavy chain constant region (CH2 or CH3), or an entire heavy chain constant region.

As referred to herein "heavy chain antibody" refers to an antibody that comprises two heavy chains and lacks the two light chains normally found in a conventional antibody. The heavy chain antibody may originate from a species of the Camelidae family or Chondrichthyes class. Heavy chain antibodies retain specific binding to an antigen in the absence of any light chain.

As referred to herein "specific binding", "specifically binds" or variations thereof refer to binding that occurs between an antibody and its target molecule that is mediated by at least one complementarity determining region (CDR) of the antibody's variable region. Binding that is between the constant region and another molecule, such as Protein A or G, for example, does not constitute specific binding.

As referred to herein "antibody fragment" refers to any portion of a conventional or heavy chain antibody that retains a capacity to specifically bind a target antigen and may include a single chain antibody, a variable region fragment of a heavy chain antibody, a nanobody, a polypeptide or an immunoglobulin new antigen receptor (IgNAR).

As referred to herein an "antibody originates from a species" when any of the CDR regions of the antibody were raised in an animal of said species. Antibodies that are raised in a certain species and then optimized by an in vitro method (e.g., phage display) are considered to have originated from that species.

As referred to herein "conventional antibody" refers to any full-sized immunoglobulin that comprises two heavy chain molecules and two light chain molecules joined together by a disulfide bond. In certain embodiments, the antibodies, compositions, feeds, products, and methods described herein do not utilize conventional antibodies.

Production System

As referred to herein, "production system" and variations thereof refer to any system that can be used to produce any physical embodiment of the invention or modified forms of the invention. Without limitation, this includes but is not limited to biological production by any of the following: bacteria, yeast, algae, arthropods, arthropod cells, plants, mammalian cells. Without limitation, biological production can give rise to antibodies that can be intracellular, periplasmic, membrane-associated, secreted, or phage-associated. Without limitation, "production system" and variations thereof also include, without limitation, any synthetic production system. This includes, without limitation, de novo protein synthesis, protein synthesis in the presence of cell extracts, protein synthesis in the presence of purified enzymes, and any other alternative protein synthesis system.

Product

As referred to herein, "product" refers to any physical embodiment of the invention or modified forms of the invention, wherein the binding of the $V_HH$ to any molecule, including itself, defines its use. Without limitation, this includes a feed, a feed additive, a nutritional supplement, a premix, a medicine, a therapeutic, a drug, a diagnostic tool, a component or entirety of an in vitro assay, a component or the entirety of a diagnostic assay (including companion diagnostic assays).

Feed Product

As referred to herein, "feed product" refers to any physical embodiment of the invention or modified forms of the invention, wherein the binding of the $V_HH$ to any molecule, including itself, defines its intended use as a product that is taken up by a host organism. Without limitation, this includes a feed, a pellet, a feed additive, a nutritional supplement, a premix, a medicine, a therapeutic or a drug.

DETAILED DESCRIPTION OF THE INVENTION

Descriptions of the invention provided are to be interpreted in conjunction with the definitions and caveats provided herein.

Domestic dogs and cats are two of the most popular household animals in the world. Despite the availability of veterinary care and canine vaccines, infectious diseases are still a common problem in dogs and cats. This is particularly true for dogs that spend significant time in kennels, shelter, and dog parks; as well as in puppies from breeding facilities. Significant pathogens affecting dogs include viruses, such as canine parvovirus, rabies, canine distemper virus, canine adenovirus, canine coronavirus, and canine parainfluenza virus, bacteria, such as members of the *Bordetella, Borrelia, Brucella, Clostridium,* and *Leptospira* genera, as well as numerous of fungi, protozoa, and parasites. Significant pathogens affecting cats include viruses, such as feline panleukopenia virus, feline immunodeficiency virus, feline leukemia virus, feline herpesvirus 1 (FHV-1), feline calicivirus, and rabies, as well as many bacteria, fungi, and parasites.

Canine parvovirus infections of dogs occur worldwide (Decaro & Buonavoglia, 2012). These infections are acquired by the fecal-oral route and cause diarrhea, vomiting, dehydration, and fever and are often fatal if untreated (Miranda & Thompson, 2016). Supportive therapy consisting of IV treatments, blood transfusions, and around the clock care (Venn et al, 2017) can be a significant financial and emotional burden to dog owners. Similarly, feline parvovirus infections of cats occur around the world. Virus particles can last in the environment for several months, are acquired by cats via the fecal-oral route, cause such symptoms as diarrhea, vomiting, fever, and immunosuppression, have high mortality rates in untreated cats, and are best treated through supportive therapy (Truyen et al, 2009)

To initiate an infection the viral capsid protein interacts with transferrin receptors on the surface of host cell prior to viral invasion (Hafenstein et al, 2007). As such peptides capable of binding the capsid protein at epitopes that are important for host cell binding should be sufficient to neutralize parvovirus infections (Yuan & Parrish, 2000).

Earlier efforts in the field of this invention rely on the host organism to generate protection against disease-causing agents. Although live attenuated canine parvovirus vaccines are available, they have some limitations. Early in life, maternally derived antibodies protect puppies from canine parvovirus; however, between weaning and successful vaccination there is a period of a few months where puppies are poorly protected (Hernández-Blanco & Catala-López, 2015). Additionally, the immunization schedule is complex, and non-compliance can lead to poor protection in adult dogs (Mylonakis et al, 2016). Similar problems exist in kittens. Jakel et al (2012) have shown that maternally derived antibodies can interfere with vaccinations and that existing vaccines, administered as recommended by the manufacturers, failed more than a third of kittens. The effectiveness of prior arts is limited by these challenges. These problems are circumvented by introducing exogenous peptides that neutralise the virulence and spread of the disease-causing agent into the host via feed without eliciting the host immune response. Moreover, the methods described herein provide scope for the adaptation and refinement of neutralising peptides, which provides synthetic functionality beyond what the host is naturally able to produce.

Antibody heavy chain variable region fragments ($V_HHs$) are small (12-15 kDa) proteins that comprise specific binding regions to antigens. When introduced into an animal, $V_HHs$ bind and neutralise the effect of disease-causing agents in situ. Owing to their smaller mass, they are less susceptible than conventional antibodies, such as previously documented IgYs, to cleavage by enzymes found in host organisms, more resilient to temperature and pH changes, more soluble, have low systemic absorption and are easier to recombinantly produce on a large scale, making them more suitable for use in animal therapeutics than conventional antibodies.

Antibodies for Preventing or Reducing Virulence (Summary)

In one aspect, the present invention provides a polypeptide or pluralities thereof comprising a $V_HH$ or $V_HHs$ that bind disease-causing agents to reduce the severity and transmission of disease between and across species. In certain embodiments, the V$_H$H is supplied to host animals. In certain embodiments, the V$_H$H is an ingredient of a product.

Binding to Reduce Virulence

In another aspect, the present invention provides a polypeptide or pluralities thereof comprising a V$_H$H or V$_H$Hs that bind disease-causing agents, and in doing so, reduce the ability of the disease-causing agent to exert a pathological function or contribute to a disease phenotype. In certain embodiments, binding of the V$_H$H(s) to the disease-causing agent reduces the rate of replication of the disease-causing agent. In certain embodiments, binding of the V$_H$H(s) to the disease-causing agent reduces the ability of the disease-causing agent to bind to its cognate receptor. In certain embodiments, binding of the V$_H$H(s) to the disease-causing agent reduces the ability of the disease-causing agent to interact with another molecule or molecules. In certain embodiments, binding of the V$_H$H(s) to the disease-causing agent reduces the ability of the disease-causing agent to reach the site of infection. In certain embodiments, binding of the V$_H$H(s) to the disease-causing agent reduces the ability of the disease-causing agent to cause cell death.

Antibodies Derived from Llamas

In a further aspect, the present invention provides a method for the inoculation of Camelid or other species with recombinant virulence factors, the retrieval of mRNA encoding V$_H$H domains from lymphocytes of the inoculated organism, the reverse transcription of mRNA encoding V$_H$H domains to produce cDNA, the cloning of cDNA into a suitable vector and the recombinant expression of the V$_H$H from the vector. In certain embodiments, the camelid can be a dromedary, camel, llama, alpaca, vicuna or guacano, without limitation. In certain embodiments, the inoculated species can be, without limitation, any organism that can produce single domain antibodies, including cartilaginous fish, such as a member of the Chondrichthyes class of organisms, which includes for example sharks, rays, skates and sawfish. In certain embodiments, the heavy chain antibody comprises a sequence set forth in Table 1. In certain embodiments, the heavy chain antibody comprises an amino acid sequence with at least 80%, 90%, 95%, 97%, or 99% identity to any sequence disclosed in Table 1. In certain embodiments, the heavy chain antibody possess a CDR1 set forth in Table 2. In certain embodiments, the heavy chain antibody possess a CDR2 set forth in Table 2. In certain embodiments, the heavy chain antibody possess a CDR3 set forth in Table 2.

TABLE 1

Unique SEQ ID NOs for VHH antibodies of this disclosure

| SEQ ID NO | NBX | Amino acid sequence | Antigen | Exemplary Antigen |
|---|---|---|---|---|
| 1 | NBX0411 | QVQLQESGGGLVQPGGSLRLSCAVSGLAFGRV AMAWYRQAPGKERELVARISSGGYTNYADSAK GRFTISRDNVKNLVYLQMNSLKFDDTAVYYCNS GWSGDYWGKGTLVTVSS | Parvovirus Capsid | Canine Parvovirus Type 2C Capsid |
| 2 | NBX0412 | QVQLQESGGGLVQAGGSLRLSCAVSGRTFSSYA MGWFRQAPGKEREYVAAINRFSGTYYADFVKG RFTISRDNAKNTVYLQMNSLKPEDTAVYYCAAS RILGLSTAREDYNYWGQGTQVTVSS | Parvovirus Capsid | Canine Parvovirus Type 2C Capsid |
| 3 | NBX0413 | QVQLQESGGGLVQAGGSLRLSCAASGHTFSSN TMAWFRQAPGKERELVAVIGWIGGSTYYADSV KGRFTISRDNTKNTVYLQMSSLKPEDTAVYYCA ADASRRRFSLQYVDYTYWGQGTQVTVSS | Parvovirus Capsid | Canine Parvovirus Type 2C Capsid |
| 4 | NBX0414 | QVQLQESGGGLVQAGGSLRLSCRASGRTFSSSS MGWFRQAPGKERDFVAAISWDGASTRYADSV KGRFTISRDNAKNTVYLQMNSLKPEDTAVYYCA ASTMDFIVLLTKWYPYWGQGTQVTVSS | Parvovirus Capsid | Canine Parvovirus Type 2C Capsid |
| 5 | NBX0415 | QVQLQESGGGLVQAGGSLRLSCAASGRTFSSYA MGWFRQAPGKEREYVAAINRFGGTYYADFVKG RFTISRDNAKNTVYLQMNSLKPEDTAVYYCAAS RILGLTTAREDYNYWGQGTQVTVSS | Parvovirus Capsid | Canine Parvovirus Type 2C Capsid |
| 6 | NBX0416 | QVQLQESGGGLVQAGGSLRLSCAASGRTFSSSS MGWFRQAPGKERDFVAAINWSGDSTRYADSV KGRFTISRDNAKSTVYLQMNSLKPEDTAVYYCA ASTMDFIVLLTKWYPYWGQGTQVTVSS | Parvovirus Capsid | Canine Parvovirus Type 2C Capsid |
| 7 | NBX0417 | QVQLQESGGGLVQPGGSLRLSCAASGSIFSINV MAWYRQAPGKEREYVASITRGGGDYYANSVK GRFTISRDNAKNAVYLQMNSLKPEDTAVYECNA QISQTISGDYRNYWGQGTQVTVSS | Parvovirus Capsid | Canine Parvovirus Type 2C Capsid |
| 8 | NBX0418 | QVQLQESGGGLVQAGGSLRLSCAASGRTFSSYA MGWFRQAPGKEREYVAAINRFGGTYYADFVKG RFTISRDNAKNTVYLQMNSLKPEDTAVYYCAAS TILGLTTVREDYNYWGQGTQVTVSS | Parvovirus Capsid | Canine Parvovirus Type 2C Capsid |

TABLE 1-continued

Unique SEQ ID NOs for VHH antibodies of this disclosure

| SEQ ID NO: | NBX | Amino acid sequence | Antigen | Exemplary Antigen |
|---|---|---|---|---|
| 9 | NBX0420 | QVQLQESGGGLVQAGGSLRLSCAASGRTFSSYG MGWFRQAPGKEREYVAVINRFGGTYYADFVKG RFTISRDNAKNTVYLQMNSLKPEDTAVYYCAAS RILGLSTAREDYNYWGQGTQVTVSS | Parvovirus Capsid | Canine Parvovirus Type 2C Capsid |
| 10 | NBX0421 | QVQLQQSGGGLVQPGGSLRLSCAVSGLAFGRY AMAWYRQAPGKERELVARISNGGYTNYADSAK GRFTISRDNVKNTVYLEMNSLKFDDTAVYYCNS GWSGNYWGKGTLVTVSS | Parvovirus Capsid | Canine Parvovirus Type 2C Capsid |
| 11 | NBX0422 | QVQLQESGGGLVQAGGSLRLSCAASGFTSSIYV MGWYRQAPGKPRDLVASINGGTTNYANSVKG RFTISRDNAKNTVSLQMNTLKPEDTAVYYCNAR HSSSWRDYWGQGTQVTVSS | Parvovirus Capsid | Canine Parvovirus Type 2C Capsid |
| 12 | NBX0423 | QVQLQESGGGLVQAGGSLRLSCAIPGRTFRNYV MGWFRQAPGKEREFVAAISRSGGSTYYSDSVK GRFTISRDNAKNTVYLQMNMLKPEDTAVYYCA ASYSIMQPTTASAMDYWGKGTLVTVSS | Parvovirus Capsid | Canine Parvovirus Type 2C Capsid |
| 13 | NBX0424 | QVQLQQSGGGSVQAGGSLSVSCAPSGRTFSW NAIGWFRQAPGKEREFVAAIRLSTGWTSYADSV KGRFSISRDAAKTTAYLQMNSLKPEDTAVYYCA ADREGSIATMTRDYEYDYWGQGTQVTVSS | Parvovirus Capsid | Canine Parvovirus Type 2C Capsid |
| 14 | NBX0425 | QVQLQESGGGLVQAGGSLRLSCAASGRTFSSYA MGWFRQAPGKEREYVAGINRFGGTYYADFVQ GRFTISRDNAKNTVYLQMNSLKPEDTAVYYCAA SRILGLTTVREDYNYWGQGTQVTVSS | Parvovirus Capsid | Canine Parvovirus Type 2C Capsid |
| 15 | NBX0426 | QVQLQESGGGLVQPGGSLRLSCAASGIGDRPYV MAWHRQAPGKQRELVATITRDGYTNYADTVK GRFVVSRDNAQNTVYLQMNYLKPADTAVYYCR AYNAYLNLGYWGQGTQVTVST | Parvovirus Capsid | Canine Parvovirus Type 2C Capsid |
| 16 | NBX0427 | QVQLQESGGGLVQAGGSLRLSCAASGITFSTFA MGWYRQAPGKQRELVAQISNDGYINYADSVK GRFTISRDNAKNTVSLQMNSLKPDDTAVYSCRA GTFYWGQGTQVTVSS | Parvovirus Capsid | Canine Parvovirus Type 2C Capsid |
| 17 | NBX0428 | QVQLQESGGGLVQAGGSLRLSCAASGSTSSINH IAWYRQAPGKQREWVATITSGGGSTYYTNSVK GRFTISRDNAKNTVYLQMNNLKPEDTAVYYCKA NQAAGNKDYWGQGTQVTVSS | Parvovirus Capsid | Canine Parvovirus Type 2C Capsid |
| 18 | NBX0429 | QVQLQQSGGGLVQAGGSLRLSCAASGRTFSSY AMGWFRQAPGKEREYVAAINRFGGTYYADFVK GRFTISRDNAKNTVYLQMNSLKPEDTAVYYCAA SGILGLSTAREDYNYWGQGTQVTVSS | Parvovirus Capsid | Canine Parvovirus Type 2C Capsid |
| 77 | NBX0430 | QVQLQQSGGGLVQAGGSLRLSCAASGLTFGSP AMAWYRQAPGKEREWVATISRGGSTYYADSV KGRFTISRDNAKNTSYLQMNSLKPEETAVYYCA AGLSSMRYDYWGQGTQVTVSS | Parvovirus Capsid | Canine Parvovirus Type 2C Capsid |
| 78 | NBX0431 | QVQLQQSGGGLVQAGGSLRLSCAASGRTFSSY AMGWFRQAPGKEREYVAGINRFGGTYYADFVK GRFTISRDNAKNTVYLQMNSLKPEDTAVYYCAA SRILGLSTAREDYNYWGQGTQVTVSS | Parvovirus Capsid | Canine Parvovirus Type 2C Capsid |
| 79 | NBX0432 | QVQLQESGGGLVQTGASLRLSCAVSGRRITDYII GWFRQAPGKEREFVGQISRSANSIIANSVKGRF TISRDNANNTVSLQMNSLKPDDTAVYLCGASSSI GVWTTSQYYDYWGQGTRVTVSS | Parvovirus Capsid | Canine Parvovirus Type 2C Capsid |

TABLE 2

Unique SEQ IDs for V$_H$H CDRs of this disclosure

| NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen | Exemplary Antigen |
|---|---|---|---|---|---|---|---|---|
| NBX0411 | GLAFGRVAM | 19 | ISSGGYT | 37 | NSGWSGDY | 55 | Parvovirus Capsid | Canine Parvovirus Type 2C Capsid |
| NBX0412 | GRTFSSYAM | 20 | INRFSGT | 38 | AASRILGLSTAREDYNY | 56 | Parvovirus Capsid | Canine Parvovirus Type 2C Capsid |
| NBX0413 | GHTFSSNTM | 21 | IGWIGGST | 39 | AADASRRRFSLQYVDYTY | 57 | Parvovirus Capsid | Canine Parvovirus Type 2C Capsid |
| NBX0414 | GRTFSSSSM | 22 | ISWDGAST | 40 | AADASRRRFSLQYVDYTY | 57 | Parvovirus Capsid | Canine Parvovirus Type 2C Capsid |
| NBX0415 | GRTFSSYAM | 20 | INRFGGT | 41 | AASRILGLTTAREDYNY | 59 | Parvovirus Capsid | Canine Parvovirus Type 2C Capsid |
| NBX0416 | GRTFSSSSM | 22 | INWSGDST | 42 | AASTMDFIVLLTKWYPY | 60 | Parvovirus Capsid | Canine Parvovirus Type 2C Capsid |
| NBX0417 | GSIFSINVM | 25 | ITRGGGD | 43 | NAQISQTISGDYRNY | 61 | Parvovirus Capsid | Canine Parvovirus Type 2C Capsid |
| NBX0418 | GRTFSSYAM | 20 | INRFGGT | 41 | AASTILGLTTVREDYNY | 62 | Parvovirus Capsid | Canine Parvovirus Type 2C Capsid |
| NBX0420 | GRTFSSYGM | 27 | INRFGGT | 41 | AASRILGLSTAREDYNY | 56 | Parvovirus Capsid | Canine Parvovirus Type 2C Capsid |
| NBX0421 | GLAFGRYAM | 28 | ISNGGYT | 46 | NSGWSGNY | 64 | Parvovirus Capsid | Canine Parvovirus Type 2C Capsid |
| NBX0422 | GFTSSIYVM | 29 | INGGTT | 47 | NARHSSSWRDY | 65 | Parvovirus Capsid | Canine Parvovirus Type 2C Capsid |
| NBX0423 | GRTFRNYVM | 30 | ISRSGGST | 48 | AASYSIMQPTTASAMDY | 66 | Parvovirus Capsid | Canine Parvovirus Type 2C Capsid |
| NBX0424 | GRTFSWNAI | 31 | IRLSTGWT | 49 | AADREGSIATMTRDYEYDY | 67 | Parvovirus Capsid | Canine Parvovirus Type 2C Capsid |
| NBX0425 | GRTFSSYAM | 20 | INRFGGT | 41 | AASRILGLTTVREDYNY | 68 | Parvovirus Capsid | Canine Parvovirus Type 2C Capsid |
| NBX0426 | GIGDRPYVM | 33 | ITRDGYT | 51 | RAYNAYLNLGY | 69 | Parvovirus Capsid | Canine Parvovirus Type 2C Capsid |
| NBX0427 | GITFSTFAM | 34 | ISNDGYI | 52 | RAGTFY | 70 | Parvovirus Capsid | Canine Parvovirus Type 2C Capsid |
| NBX0428 | GSTSSINHI | 35 | ITSGGGST | 53 | KANQAAGNKDY | 71 | Parvovirus Capsid | Canine Parvovirus Type 2C Capsid |
| NBX0429 | GRTFSSYAM | 20 | INRFGGT | 41 | AASGILGLSTAREDYNY | 72 | Parvovirus Capsid | Canine Parvovirus Type 2C Capsid |

TABLE 2-continued

Unique SEQ IDs for V$_H$H CDRs of this disclosure

| NBX | CDR1 Amino Acid Sequence | CDR1 SEQ ID NO: | CDR2 Amino Acid Sequence | CDR2 SEQ ID NO: | CDR3 Amino Acid Sequence | CDR3 SEQ ID NO: | Antigen | Exemplary Antigen |
|---|---|---|---|---|---|---|---|---|
| NBX0430 | GLTFGSPAM | 80 | ISRGGST | 83 | AAGLSSMRYDY | 86 | Parvovirus Capsid | Canine Parvovirus Type 2C Capsid |
| NBX0431 | GRTFSSYAM | 20 | INRFGGT | 41 | AASRILGLSTAREDYNY | 56 | Parvovirus Capsid | Canine Parvovirus Type 2C Capsid |
| NBX0432 | GRRITDYII | 82 | ISRSANS | 85 | GASSSIGVWTTSQYYDY | 88 | Parvovirus Capsid | Canine Parvovirus Type 2C Capsid |

Antibodies Recombinantly Expressed

In another aspect, the present invention provides a method for producing V$_H$H in a suitable producing organism. Suitable producing organisms include, without limitation, bacteria, yeast and algae. In certain embodiments, the producing bacterium is *Escherichia coli*. In certain embodiments, the producing bacterium is a member of the *Bacillus* genus. In certain embodiments, the producing bacterium is a probiotic. In certain embodiments, the yeast is *Pichia pastoris*. In certain embodiments, the yeast is *Saccharomyces cerevisiae*. In certain embodiments, the alga is a member of the *Chlamydomonas* or *Phaeodactylum* genera.

Antibodies Added to Feed

In yet another aspect, the present invention provides a polypeptide or pluralities thereof comprising a V$_H$H or V$_H$Hs that bind disease-causing agents and are administered to host animals via any suitable route as part of a feed product. In certain embodiments, the animal is selected from the list of host animals described, with that list being representative but not limiting. In certain embodiments, the route of administration to a recipient animal can be, but is not limited to: introduction to the alimentary canal orally or rectally, provided to the exterior surface (for example, as a spray or submersion), provided to the medium in which the animal dwells (including air based media), provided by injection, provided intravenously, provided via the respiratory system, provided via diffusion, provided via absorption by the endothelium or epithelium, or provided via a secondary organism such as a yeast, bacterium, algae, bacteriophages, plants and insects. In certain embodiments, the host is from the order Carnivora. In certain embodiments, the host is from the order Canidae. In certain embodiments, the host is a domestic dog, wolf, coyote, fox, jackal, or dingo. In certain embodiments, the host is a domestic dog. In certain embodiments, the host is from the family Felidae. In certain embodiments, the host is a domestic cat, a wild cat, leopard, tiger, jaguar, lion, serval, caracal, ocelot, margay, kodkod, oncilla, bobcat, lynx, cheetah, cougar, or jaguarundi. In certain embodiments, the host is a domestic cat. In certain embodiments the host is a non-canine and non-feline species. In certain embodiments the non-canine and non-feline species is a mink, skunk or raccoon.

Feed Product

In a further aspect, the present invention provides a polypeptide or pluralities thereof comprising a V$_H$H or V$_H$Hs that bind disease-causing agents and are administered to host animals in the form of a product. The form of the product is not limited. In certain embodiments, the product is feed, pellet, nutritional supplement, premix, therapeutic, medicine, or feed additive, but is not limited to these forms.

Feeding Dosage

In a further aspect, the present invention provides a polypeptide or pluralities thereof comprising a V$_H$H or V$_H$Hs that bind disease-causing agents and are administered to host animals as part of a product at any suitable dosage regime. In practice, the suitable dosage is the dosage at which the product offers any degree of protection against a disease-causing agent, and depends on the delivery method, delivery schedule, the environment of the recipient animal, the size of the recipient animal, the age of the recipient animal and the health condition of the recipient animal among other factors. In certain embodiments, V$_H$Hs are administered to recipient animals at a concentration in excess of 1 mg/kg of body weight. In certain embodiments, V$_H$Hs are administered to recipient animals at a concentration in excess of 5 mg/kg of body weight. In certain embodiments, V$_H$Hs are administered to recipient animals at a concentration in excess of 10 mg/kg of body weight. In certain embodiments, V$_H$Hs are administered to recipient animals at a concentration in excess of 50 mg/kg of body weight. In certain embodiments, V$_H$Hs are administered to recipient animals at a concentration in excess of 100 mg/kg of body weight. In certain embodiments, V$_H$Hs are administered to recipient animals at a concentration less than 1 mg/kg of body weight. In certain embodiments, V$_H$Hs are administered to recipient animals at a concentration less than 500 mg/kg of body weight. In certain embodiments, V$_H$Hs are administered to recipient animals at a concentration less than 100 mg/kg of body weight. In certain embodiments, V$_H$Hs are administered to recipient animal at a concentration less than 50 mg/kg of body weight. In certain embodiments, V$_H$Hs are administered to recipient animals at a concentration less than 10 mg/kg of body weight.

Feeding Frequency

In a further aspect, the present invention provides a polypeptide or pluralities thereof comprising a V$_H$H or V$_H$Hs that bind disease-causing agents and are administered to host animals as part of a product at any suitable dosage frequency. In practice, the suitable dosage frequency is that at which the product offers any protection against a disease-causing agent, and depends on the delivery method, delivery schedule, the environment of the recipient animal, the size of the recipient animal, the age of the recipient animal and the health condition of the recipient animal, among other factors. In certain embodiments, the dosage frequency can be but is not limited to: constantly, at consistent specified frequencies under an hour, hourly, at specified frequencies throughout a 24-hour cycle, daily, at specified frequencies throughout a week, weekly, at specified frequencies throughout a month, monthly, at specified frequencies throughout a year, annually, at specified frequencies greater than 1 year.

Feed Additives

In a further aspect, the present invention provides a polypeptide or pluralities thereof comprising a $V_HH$ or $V_HHs$ that bind disease-causing agents and are administered to host animals as part of a product that also comprises other additives or coatings. In practice, the most suitable coating or additive depends on the method of delivery, the recipient animal, the environment of the recipient, the dietary requirements of the recipient animal, the frequency of delivery, the age of the recipient animal, the size of the recipient animal, the health condition of the recipient animal In certain embodiments, these additives and coatings can include but are not limited to the following list and mixtures thereof: meat, a meat by-product, bone meal, fish, fish meal, egg, egg by-product, a vitamin, vegetables, plant matter, plant extracts, an amino acid, a dye, an antibiotic, an antiviral, a hormone, an antimicrobial peptide, a steroid, a prebiotic, a probiotic, a bacteriophage, chitin, chitosan, B-1,3-glucan, vegetable extracts, peptone, krill, algae, B-cyclodextran, alginate, gum, tragacanth, pectin, gelatin, an additive spray, a toxin binder, a short chain fatty acid, a medium chain fatty acid, an omega-3 fatty acid, yeast, a yeast extract, a plant extract, sugar, a digestive enzyme, a digestive compound, an essential mineral, carnitine, glucosamine, an essential salt, fibre, a preservative, a stabilizer, a natural flavour, an artificial flavour, or water.

Non-Feed Uses

In a further aspect, the present invention provides a polypeptide or pluralities thereof comprising a $V_HH$ or $V_HHs$ that bind disease-causing agents, and can be used in a non-feed use, such as but not limited to: a diagnostic kit, an enzyme-linked immunoabsorbent assay (ELISA), a western blot assay, an immunofluorescence assay, or a fluorescence resonance energy transfer (FRET) assay, in its current form and/or as a polypeptide conjugated to another molecule. In certain embodiments, the conjugated molecule is can be but is not limited to: a fluorophore, a chemiluminescent substrate, an antimicrobial peptide, a nucleic acid or a lipid.

Antigens

In a further aspect, the present invention provides a polypeptide or pluralities thereof comprising a $V_HH$ or $V_HHs$ that bind disease-causing agents, produced by a virus of the family Parvoviridae. In certain embodiments, the Parvoviridae virus refers to both current and reclassified viruses. In certain embodiments, the Parvoviridae virus is canine parvovirus type 2. In certain embodiments, the Parvoviridae virus is feline panleukopenia virus.

In certain embodiments, the $V_HH$ or plurality thereof is capable of binding to one or more disease-causing agents, originating from the same or different viruses. In certain embodiments, the disease-causing agent is a polypeptide with 80% or greater amino acid sequence identity to canine parvovirus type 2C capsid protein (SEQ ID NO: 73). In certain embodiments, the disease-causing agent is a polypeptide with 80% or greater amino acid sequence identity to canine parvovirus type 2A capsid protein (SEQ ID NO: 75). In certain embodiments, the disease-causing agent is a polypeptide with 80% or greater amino acid sequence identity to canine parvovirus type 2B capsid protein (SEQ ID NO: 76). In certain embodiments, the disease-causing agent is the canine parvovirus type 2 virus. In certain embodiments, the disease-causing agent is a polypeptide with 80% or greater amino acid sequence identity to feline panleukopenia virus capsid protein (SEQ ID NO: 74). In certain embodiments, the disease-causing agent is the feline panleukopenia virus. In certain embodiments, the disease-causing agent is a polypeptide with 80% or greater amino acid sequence identity to mink enteritis virus capsid protein (SEQ ID NO: 89). In certain embodiments, the disease-causing agent is the mink enteritis virus. In certain embodiments, the disease-causing agent is a polypeptide with 80% or greater amino acid sequence identity to ungulate protoparvovirus 1 capsid protein (SEQ ID NO: 90). In certain embodiments, the disease-causing agent is the ungulate protoparvovirus 1. In certain embodiments, the disease-causing agent is a polypeptide with 80% or greater amino acid sequence identity to mouse protoparvovirus 1 capsid protein (SEQ ID NO: 91). In certain embodiments, the disease-causing agent is the mouse protoparvovirus 1.

Antigen Sequences

Canine Parvovirus Type 2C Capsid Protein (SEQ ID NO: 73)

AIW67511.1 VP1 [Canine parvovirus 2c]

```
MAPPAKRARRGLVPPGYKYLGPGNSLDQGEPTNPSDAAAKEHDEAYAAY
LRSGKNPYLYFSPADQRFIDQTKDAKDWGGKIGHYFFRAKKAIAPVLTD
TPDHPSTSRPTKPTKRSKPPPHIFINLAKKKKAGAGQVKRDNLAPMSDG
AVQPDGGQPAVRNERATGSGNGSGGGGGGSGGVGISTGTFNNQTEFKF
LENGWVEITANSSRLVHLNMPESENYRRVVVNNLDKTAVNGNMALDDTH
AQIVTPWSLVDANAWGVWFNPGDWQLIVNTMSELHLVSFEQEIFNVVLK
TVSESATQPPTKVYNNDLTASLMVALDSNNTMPFTPAAMRSETLGFYPW
KPTIPTPWRYYFQWDRTLIPSHTGTSGTPTNIYHGTDPDDVQFYTIENS
VPVHLLRTGDEFATGTFFFDCKPCRLTHTWQTNRALGLPPFLNSLPQAE
GGTNFGYIGVQQDKRRGVTQMGNTNYITEATIMRPAEVGYSAPYYSFEA
STQGPFKTPIAAGRGGAQTDENQAADGDPRYAFGRQHGQKTTTTGETPE
RFTYIAHQDTGRYPEGDWIQNINFNLPVTEDNVLLPTDPIGGKTGINYT
NIFNTYGPLTALNNVPPVYPNGQIWDKEFDTDLKPRLHVNAPFVCQNNC
PGQLFVKVAPNLTNEYDPDASANMSRIVTYSDFWWKGKLVFKAKLRASH
TWNPIQQMSINVDNQFNYVPSNIGGMKIVYEKSQLAPRKLY
```

Feline Panleukopenia Virus Capsid Protein (SEQ ID NO: 74)

AAC37928.1 capsid protein VP1 [Feline panleukopenia virus]

```
MAPPAKRARRGLVPPGYKYLGPGNSLDQGEPTNPSDAAAKEHDEAYAAY
LRSGKNPYLYFSPADQRFIDQTKDAKDWGGKIGHYFFRAKKAIAPVLTD
TPDHPSTSRPTKPTKRSKPPPHIFINLAKKKKAGAGQVKRDNLAPMSDG
AVQPDGGQPAVRNERATGSGNGSGGGGGGSGGVGISTGTFNNQTEFKF
LENGWVEITANSSRLVHLNMPESENYKRVVVNNMDKTAVKGNMALDDIH
VQIVTPWSLVDANAWGVWFNPGDWQLIVNTMSELHLVSFEQEIFNVVLK
TVSESATQPPTKVYNNDLTASLMVALDSNNTMPFTPAAMRSETLGFYPW
```

-continued
KPTIPTPWRYYFQWDRTLIPSHTGTSGTPTNVYHGTDPDDVQFYTIENS

VPVHLLRTGDEFATGTFFFDCKPCRLTHTWQTNRALGLPPFLNSLPQSE

GATNFGDIGVQQDKRRGVTQMGNTDYITEATIMRPAEVGYSAPYYSFEA

STQGPFKTPIAAGRGGAQTDENQAADGDPRYAFGRQHGQKTTTTGETPE

RFTYIAHQDTGRYPEGDWIQNINFNLPVTNDNVLLPTDPIGGKTGINYT

NIFNTYGPLTALNNVPPVYPNGQIWDKEFDTDLKPRLHVNAPFVCQNNC

PGQLFVKVAPNLTNEYDPDASANMSRIVTYSDFWWKGKLVFKAKLRASH

TWNPIQQMSINVDNQFNYVPNNIGAMKIVYEKSQLAPRKLY

Canine Parvovirus Type 2A Capsid Protein (SEQ ID NO: 75)
ALC79696.1 VP1 [Canine parvovirus 2a]

MAPPAKRARRGLVPPGYKYLGPGNSLDQGEPTNPSDAAAKEHDEAYAAY

LRSGKNPYLYFSPADQRFIDQTKDAKDWGGKIGHYFFRAKKAIAPVLTD

TPDHPSTSRPTKPTKRSRPPPHIFINLAKKKKAGAGQVKRDNLAPMSDG

AVQPDGGQPAVRNERATGSGNGSGGGGGGGSGGVGISTGTFNNQTEFKF

LENGWVEITANSSRLVHLNMPESENYRRVVVNNLDKTAVNGNMALDDTH

AQIVTPWSLVDANAWGVWFNPGDWQLIVNTMSELHLVSFEQEIFNVVLK

TVSESATQPPTKVYNNDLTASLMVALDSNNTMPFTPAAMRSETLGFYPW

KPTIPTPWRYYFQWDRTLIPSHTGTSGTPTNIYHGTDPDDVQFYTIENS

VPVHLLRTGDEFATGTFYFDCKPCRLTHTWQTNRALGLPPFLNSLPQAE

GGTNFGYIGVQQDKRRGVTQMGNTNIITEATIMRPAEVGYSAPYYSFEA

STQGPFKTPIAAGRGGAQTDENQAADGDPRYAFGRQHGQKTTTTGETPE

RFTYIAHQDTGRYPEGDWIQNINFNLPVTNDNVLLPTDPIGGKAGINYT

NIFNTYGPLTALNNVPPVYPNGQIWDKEFDTDLKPRLHVNAPFVCQNNC

PGQLFVKVAPNLTNEYDPDASANMSRIVTYSDFWWKGKLVFKAKLRASH

TWNPIQQMSINVDNQFNYVPSNIGGMKIVYEKSQLAPRKLY

Canine Parvovirus Type 2B Capsid Protein (SEQ ID NO: 76)
ALC79660.1 VP1 [Canine parvovirus 2b]

MAPPAKRARRGLVPPGYKYLGPGNSLDQGEPTNPSDAAAKEHDEAYAAY

LRSGKNPYLYFSPADQRFIDQTKDAKDWGGKIGHYFFRAKKAIAPVLTD

TPDHPSTSRPTKPTKRSRPPPHIFINLAKKKKAGAGQVKRDNLAPMSDG

AVQPDGGQPAVRNERATGSGNGSGGGGGGGSGGVGISTGTFNNQTEFKF

LENGWVEITANSSRLVHLNMPESENYRRVVVNNLDKTAVNGNMALDDTH

AQIVTPWSLVDANAWGVWFNPGDWQLIVNTMSELHLVSFEQEIFNVVLK

TVSESATQPPTKVYNNDLTASLMVALDSNNTMPFTPAAMRSETLGFYPW

KPTIPTPWRYYFQWDRTLIPSHTGTSGTPTNIYHGTDPDDVQFYTIENS

VPVHLLRTGDEFATGTFYFDCKPCRLTHTWQTNRALGLPPFLNSLPQAE

GGTNFGYIGVQQDKRRGVTQMGNTNIITEATIMRPAEVGYSAPYYSFEA

STQGPFKTPIAAGRGGAQTDENQAADGDPRYAFGRQHGQKTTTTGETPE

RFTYIAHQDTGRYPEGDWIQNINFNLPVTDDNVLLPTDPIGGKAGINYT

NIFNTYGPLTALNNVPPVYPNGQIWDKEFDTDLKPRLHVNAPFVCQNNC

PGQLFVKVAPNLTNEYDPDASANMSRIVTYSDFWWKGKLVFKAKLRASH

TWNPIQQMSINVDNQFNYVPSNIGGMKIVYEKSQLAPRKLY

Mink Enteritis Virus (SEQ ID NO: 89)
AAA87193.1 VP1 [Mink enteritis virus]

MAPPAKRARRGLVPPGYKYLGPGNSLDQGEPTNPSDAAAKEHDEAYAAY

LRSGKNPYLYFSPADQRFIDQTKDAKDWGGKIGHYFFRDKKAIAPVLSD

TPDHPSTSRPAKPSKRCKPPPHIFINLAKKKNAGAAQVKRDNLAPMSDG

AVQPDGGQPAVRNERATGSGNGSGGGGGGSGGVGISTGTFNNQTEFKF

LENGWVEITANSSRLVHLNMPESENYKRVVVNNMDKTAVKGNMALDDTH

VQIVTPWSLVDANAWGVWFNPGDWQLIVNTMSELHLVSFEQEIFNVVLK

TVSESATQPPTKVYNNDLTASLMVALDSNNTMPFTPAAMRSETLGFYPW

KPTIPTPWRYYFQWDRTLIPSHTGTSGTPTNIYHGTDPDDVQFYTIENS

VPVHLLRTGDEFATGTFFFDCKPCRLTHTWQTNRALGLPPFLNSLPQSE

GATNFGDIGVQQDKRRGVTQMGNTDYITEATIMRPAEVGYSAPYYSFEA

STQGPFKTPIAAGRGGAQTDENQAADGDPRYAFGRQHGQKTTTTGETPE

RFTYIAHQDTGRYPEGDWIQNINFNLPVTNDNVLLPTDPIGGKTGINYT

NIFNTYGPLTALNNVPPVYPNGQIWDKEFDTDLKPRLHVNAPFVCHNNC

PGQLFVKVAPNLTNEYDPDASANMSRIVTYSDFWWKGKLVFKAKLRASH

TWNPIQQMSINVDNQFNYLPNNIGAMKIVYEKSQLAPRKLY

EXAMPLES

The following illustrative examples are representative of the embodiments of the applications, systems and methods described herein and are not meant to be limiting in any way.

While preferred embodiments of the present invention are shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Production of Antigens

Recombinant parvovirus capsid can be purified from an insect expression system. For example, capsid protein can be expressed at 26° C. in *Spodoptera frugiperda* 9 (Sf9) cells cultured in suspension in shaker flasks. Cells are pelleted, frozen, thawed, and then lysed by osmotic shock in a 25 mM sodium bicarbonate solution. The lysate is cleared by centrifugation at 10,000×g for 30 minutes at 4° C. Virus-like particles are precipitated from the supernatant using 20% ammonium sulfate and removed by centrifugation. The pelleted virus-like particles are resuspended in phosphate-buffered saline, pH 7.4 (PBS). Confirmation of virus-like particle production is obtained via electron microscopy and hemagglutination of porcine erythrocytes. The purified virus-like particles are stored at −80° C.

Production of NBXs and Panning

Llama Immunization

A llama is immunized with purified disease-causing agents, these can include recombinantly expressed parvovirus capsid or parvovirus viral particles, which may be accompanied by adjuvants. The llama immunization is performed using 100 μg of antigen at days 0, 21, 42, and 63. At the time of injection, the antigen is thawed, and the volume increased to 1 ml with PBS. The 1 ml antigen-PBS mixture is then mixed with 1 ml of Complete Freund's adjuvant (CFA) or Incomplete Freund's adjuvant (IFA) for a total of 2 ml. A total of 2 ml is immunized per injection. Whole llama blood and sera are then collected from the immunized animal on days 0, 28, 49, 70. Sera from days 28, 49 and 70 are then fractionated to separate $V_HH$ from conventional antibodies. ELISA can be used to measure reactivity against target antigens in polyclonal and $V_HH$-enriched fractions. Lymphocytes are collected from sera taken at days 28, 49, and 70.

Panning

RNA isolated from purified llama lymphocytes is used to generate cDNA for cloning into phagemids. The resulting phagemids are used to transform *E. coli* TG-1 cells to generate a library of expressed $V_HH$ genes. The phagemid library size can be ~2.5×10$^7$ total transformants and the estimated number of phagemid containing $V_HH$ inserts can be estimated to be >90%. High affinity antibodies are then selected by panning against the antigens used for llama immunization. Two rounds of panning are performed and antigen-binding clones arising from round 2 are identified using phage ELISA. Antigen-binding clones are sequenced, grouped according to their CDR regions, and prioritized for soluble expression in *E. coli* and antibody purification.

Figure 3:
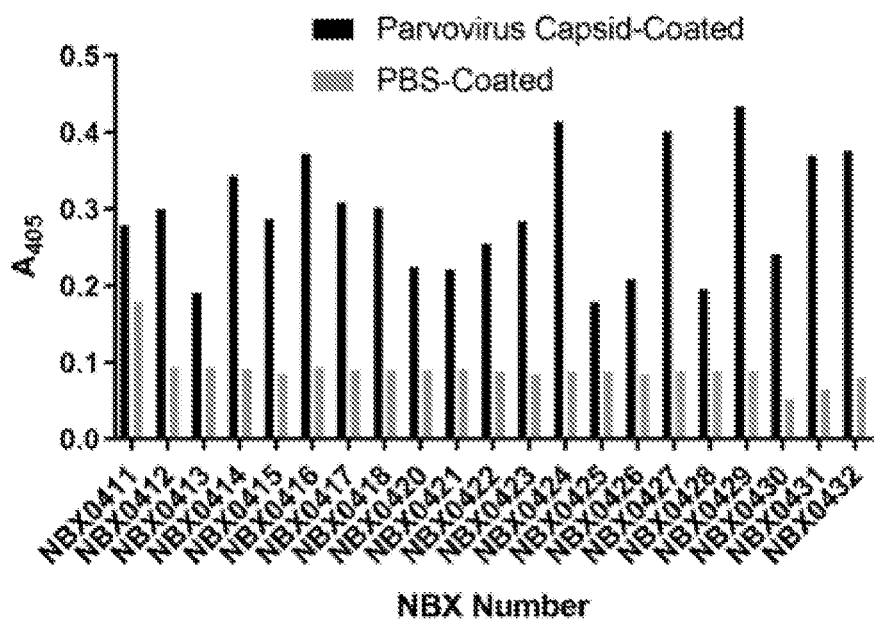
FIG. 3 shows phage ELISA binding data for $V_HH$ antibodies of this disclosure.

FIG. 3 shows the phage ELISA results for antibodies of this disclosure. Black bars show binding to wells coated with the antigen specified in Tables 1 and 2 dissolved in phosphate-buffered saline (PBS). Grey bars are negative controls that show binding to wells coated with PBS only. In all cases binding to the antigen target is at least 50% above binding to the PBS-coated wells.

Purification of $V_H$Hs from *E. coli*

TEV protease-cleavable, 6×His-thioredoxin-NBX fusion proteins are expressed in the cytoplasm of *E. coli* grown in autoinducing media (Formedium) for 24 hours at 30° C. Bacteria are collected by centrifugation, resuspended in buffer A (10 mM HEPES, pH 7.5, 250 mM NaCl, 20 mM Imidazole) and lysed using sonication. Insoluble material is removed by centrifugation and the remaining soluble fraction is applied to a HisTrap column (GE Biosciences) pre-equilibrated with buffer A. The protein is eluted from the column using an FPLC with a linear gradient between buffer A and buffer B (10 mM HEPES, pH 7.5, 500 mM NaCl, 500 mM Imidazole). The eluted protein is dialyzed overnight in the presence of TEV protease to buffer C (10 mM HEPES, pH 7.5, 500 mM NaCl). The dialyzed protein is applied to a HisTrap column (GE Biosciences) pre-equilibrated with buffer C. 6×His-tagged TEV and 6×His-tagged thioredoxin are bound to the column and highly purified NBX is collected in the flow through. NBX proteins are dialyzed overnight to PBS and concentrated to ~10 mg/ml.

Purification of $V_H$Hs from *P. pastoris*

*Pichia pastoris* strain GS115 with constructs for the expression and secretion of 6×His-tagged $V_H$H are grown for 5 days at 30° C. with daily induction of 0.5% (vol/vol) methanol. Yeast cells are removed by centrifugation and the NBX-containing supernatant is spiked with 10 mM imidazole. The supernatant is applied to a HisTrap column (GE Biosciences) pre-equilibrated with buffer A (10 mM HEPES, pH 7.5, 500 mM NaCl). The protein is eluted from the column using an FPLC with a linear gradient between buffer A and buffer B (10 mM HEPES, pH 7.5, 500 mM NaCl, 500 mM Imidazole). NBX proteins are dialyzed overnight to PBS and concentrated to ~10 mg/ml.

NBX Inhibition of Red Blood Cell Hemagglutination by Parvovirus Capsid

Recombinantly expressed canine parvovirus capsid protein is diluted to approximately 1 nM in PBS and 80 μL of capsid solution or PBS buffer is added to triplicate wells of a 96-well microtitre plate. 10 μL of various NBX solutions are added to the capsid solution, yielding final NBX concentrations of 0, 1, 3, 9, 27, 81, 243, 729, or 2187 nM. Capsid/NBX mixtures are incubated at 4° C. for 30 minutes. 10 μL of a 10% solution of porcine red blood cells (RBC) are added to the wells and mixed. Capsid/NBX/RBC mixtures are incubated at 4° C. for 60 minutes and the plate is photographed. In the absence of capsid protein, the RBCs sink to the bottom of the well. In the presence of capsid protein, the RBCs are agglutinated and remain suspended in the solution of the well. In the presence of neutralizing NBXs, the capsid fails to agglutinate the RBCs and the RBCs sink to the bottom of the well. The minimum hemagglutination inhibition concentration (MHIC) is the lowest concentration of NBX that completely inhibits capsid hemagglutination or RBCs in all three triplicate wells tested.

Table 3 indicates, for all NBXs tested, whether the NBX can neutralize the hemagglutination ability of parvovirus capsid with MHIC values lower than 1 μM or 100 nM

TABLE 3

Summary table for NBXs that neutralize hemagglutination of porcine RBCs by canine parvovirus capsid

| NBX Number | MHIC <1 μM | MHIC <100 nM |
|---|---|---|
| NBX0411 | Yes | Yes |
| NBX0412 | No | No |
| NBX0413 | No | No |
| NBX0414 | Yes | Yes |
| NBX0415 | No | No |
| NBX0416 | Yes | Yes |
| NBX0417 | Yes | No |
| NBX0418 | Yes | Yes |
| NBX0420 | No | No |
| NBX0421 | Yes | Yes |
| NBX0422 | No | No |
| NBX0423 | No | No |
| NBX0424 | Yes | Yes |
| NBX0425 | No | No |
| NBX0426 | No | No |
| NBX0427 | No | No |
| NBX0428 | Yes | Yes |
| NBX0429 | No | No |
| NBX0430 | Yes | No |
| NBX0431 | No | No |

NBX Inhibition of Canine Parvovirus Invasion of MDCK Cells

Madin-Darby Canine Kidney (MDCK) cells are seeded at $4\times10^4$ cells per well in a 96-well plate the day before infection. The next day, NBXs are diluted to 50 μM in Eagle's Minimum Essential Medium (EMEM). Canine Parvovirus Type 2 (CPV2) stock is diluted 100-fold in EMEM. NBXs and CPV2 are mixed and the final concentration of NBX is 5 μM. The NBX/CPV2 mixtures are incubated at 37° C. for 60 minutes. Remove media from the cells, add 30 μl of NBX/CPV2 mixtures to the cells, and incubate at 37°

C. for 90 minutes. Rock the plate every 15 minutes during the 90-minute infection. Add 70 µl of Dulbecco's Modified Eagle Medium with 2% FBS to the cells and incubate at 37° C. for 24 hours. Fix cells with 4% paraformaldehyde (in PBS) for 60 minutes at room temperature, stop fixation with 0.1 M glycine for 15 minutes. Permeabilize cells with 0.1% Triton-X100 (in PBS) for 30 minutes, and block with 5% milk in PBS-T (0.05% Tween-20) for 60 minutes at room temperature. For detection, incubate with mouse anti-CPV2 antibodies for 60 minutes and HRP-conjugated anti-mouse antibodies for 60 minutes. Incubate with TMB substrate for 30 minutes and stop the reaction with 1 N HCl. Read the absorbance at 450 nm.

Table 4 indicates for all NBXs tested, whether the NBX can neutralize the invasion of MDCK cells by >50% at a concentration of 5 mM.

TABLE 4

Summary table for NBXs that prevent invasion by canine parvovirus

| NB

What is claimed is:

1. A polypeptide comprising at least one variable region fragment of a heavy chain antibody ($V_HH$), wherein the at least one $V_HH$ specifically binds a parvovirus, and wherein the polypeptide:
   a) prevents red blood cell hemagglutination by canine parvovirus type 2C capsid at a concentration lower than 100 nM, and the at least one $V_HH$ comprises an amino acid sequence at least 95% identical to an amino acid sequence of any one of SEQ ID Nos: 1, 4, 6, 8, 10, 13 or 17;
   b) prevents red blood cell hemagglutination by canine parvovirus type 2C capsid at a concentration lower than 1 μM, and the at least one $V_HH$ comprises an amino acid sequence at least 95% identical to an amino acid sequence of any one of SEQ ID Nos 1, 4, 6, 7, 8, 10, 13, 17 or 77; or
   c) reduces invasion of Madin-Darby canine kidney (MDCK} cells by canine parvovirus by >50% at 5 μM, and the at least one $V_HH$ comprises an amino acid sequence at least 95% identical to an amino acid sequence of any one of SEQ ID Nos: 1, 4, 10, 15 or 17.

2. The polypeptide of claim 1, wherein the polypeptide comprises a plurality of the $V_HH$.

3. The polypeptide of claim 1, wherein the at least one $V_HH$ specifically binds a canine parvovirus virulence factor.

4. The polypeptide of claim 1, wherein the at least one $V_HH$ specifically binds an antigen or polypeptide at least 80% identical to SEQ ID NOs: 73, 74, 75, 76 or 89.

5. The polypeptide of claim 1, wherein the at least one $V_HH$ binds to a swine parvovirus.

6. The polypeptide of claim 1, wherein the polypeptide is formulated for introduction to the alimentary canal orally or rectally.

* * * * *